(12) United States Patent
Ito et al.

(10) Patent No.: US 7,404,945 B2
(45) Date of Patent: Jul. 29, 2008

(54) METHOD OF EVALUATING PHARMACOLOGICAL EFFECTS OF MEDICINE

(75) Inventors: Asuka Ito, Tokyo (JP); Tadashi Kohno, Tokyo (JP); Isaburo Hosoi, Tokyo (JP); Junko Hirayama, Tokyo (JP); Kenji Maeda, Tokyo (JP)

(73) Assignee: Tokyo Gas Company Limited, Tokyo (JP)

( * ) Notice: Subject to any disclaimer, the term of this patent is extended or adjusted under 35 U.S.C. 154(b) by 356 days.

(21) Appl. No.: 10/503,557

(22) PCT Filed: Feb. 20, 2003

(86) PCT No.: PCT/JP03/01868

§ 371 (c)(1),
(2), (4) Date: Aug. 2, 2004

(87) PCT Pub. No.: WO03/071271

PCT Pub. Date: Aug. 28, 2003

(65) Prior Publication Data

US 2005/0079564 A1   Apr. 14, 2005

(30) Foreign Application Priority Data

Feb. 21, 2002 (JP) ............................. 2002-044526
Feb. 21, 2002 (JP) ............................. 2002-044791

(51) Int. Cl.
*A61K 51/00* (2006.01)

(52) U.S. Cl. .................... 424/1.81; 424/1.11; 424/1.17; 424/1.37; 424/9.2

(58) Field of Classification Search ................ 424/1.81, 424/1.11, 1.17, 1.37, 9.2
See application file for complete search history.

(56) References Cited

U.S. PATENT DOCUMENTS 5,625,125 A    4/1997   Bennett et al.
6,284,219 B1 *  9/2001  Ajami ...................... 424/1.11
2002/0159950 A1 * 10/2002  Wagner .................... 424/1.81

FOREIGN PATENT DOCUMENTS

EP           0966975 A      12/1999
WO       WO-00/34791 A      6/2000
WO       WO-00/53800 A      9/2000

OTHER PUBLICATIONS

Buehring Y. et al. Folate Deficiency in the Livers of Diethylnitrosamine Treated Rats. Cancer Research 36:2775-9, Aug. 1976.*
Fink, C. et al., "Design and synthesis of potent thiol-based inhibitors of endothelin converting enzyme-1" Bioorganic & Medicinal Chemistry Letters, Oxford, GB, vol. 10, No. 17, Sep. 2000, pp. 2037-2039.
Supplemental European Search Report dated Feb. 4, 2008 for Application No. 03705358.4-2404 PCT/JP301868.

* cited by examiner

*Primary Examiner*—Ralph Gitomer
(74) *Attorney, Agent, or Firm*—Finnegan, Henderson, Farabow, Garrett & Dunner, LLP

(57) ABSTRACT

A diagnostic reagent for use in the evaluation of a pharmacological effect of a medicine containing a pharmaceutical agent including an enzyme, an enzyme inhibitor or a receptor ligand or a prodrug of the pharmaceutical agent is provided. Further, a method of screening pharmaceutical agents each comprising an enzyme, an enzyme inhibitor or a receptor ligand and/or prodrugs of the pharmaceutical agents is provided.

26 Claims, 16 Drawing Sheets

METHOD OF EVALUATING PHARMACOLOGICAL EFFECTS OF MEDICINE

CROSS-REFERENCE TO PRIOR APPLICATION

This is a U.S. national phase application under 35 U.S.C. §371 of International Patent Application No. PCT/JP03/01868 filed Feb. 20, 2003, and claims the benefit of Japanese Patent Application Nos. 2002-44526 filed Feb. 21, 2002 and 2002-44791 filed Feb. 21, 2002 which are incorporated by reference herein. The International Application was published in Japanese on Aug. 28, 2003 as WO 03/071271 A1 under PCT Article 21(2).

TECHNICAL FIELD

The present invention relates to a diagnostic reagent for evaluating the pharmacological effect of a medicine, and a method and a reagent for screening pharmaceutical agents each comprising an enzyme, an enzyme inhibitor or a receptor ligand and/or prodrugs of the pharmaceutical agents for one or ones having high medicative efficacy and/or a small side effect.

BACKGROUND OF THE INVENTION

The pharmacological effect of a medicine has been determined based on the change in clinical conditions (improvement or occurrence of a side effect).

The determination based on clinical conditions is possible only after a medicine is administered for a certain period of time.

Blood level monitoring has also been utilized in which the pharmacological effect of a medicine is evaluated indirectly by determining whether the blood level of a pharmaceutical agent derived from the medicine falls within the therapeutic range or the safe range that is obtained empirically. However, this method only takes effect on the precondition that there is a good correlation between the pharmacological effect and the blood level to some extent and that the therapeutic range or the safe range is clearly defined ("Hyojun-yakurigaku" (Standard Textbook of Pharmacology) 5th edition, edited by Akio Ebihara (1997) p.31), and moreover the method is merely indirect as the method for evaluating a pharmacological effect.

An object of the present invention is to evaluate the pharmacological effect of a medicine by providing a diagnostic reagent for determining accurately within a short time the degree of enhancement or inhibition of the function of a target (e.g., a bioenzyme or receptor) for the medicine upon the administration of the medicine.

In the screening of therapeutic compounds, a compound having as higher a therapeutic effect and as smaller side effect as possible is selected. Most of medicines exert the pharmacological effects by inhibiting or enhancing the function of their targets (e.g., bioenzymes or receptors). Accordingly, the pharmacological effect of a medicine can be evaluated by determining the degree of inhibition or enhancement of the function of a target for the medicine.

At present, the degree of inhibition or enhancement of the function of a target is evaluated in vitro. In recent years, an in vitro assay system called "HTS" (high throughput screening) which enables the processing of a large number of samples has been most common. This method uses a high density plate such as a 96-well, 384-well or 1536-well plate, utilizes techniques such as automation to great advantage, and can evaluate the pharmacological effect on a large number of samples up to hundreds of thousands at a high rate.

However, a result given in an in vitro evaluation does not always agree with a result given when a medicine is administered to an individual.

The only way to know the result of administering a medicine to an individual is to observe the change in clinical conditions (improvement or occurrence of a side effect) in the individual.

Accordingly, an object of the present invention is to provide a method and a reagent for screening pharmaceutical agents and/or prodrugs thereof for one or ones having high medicative efficacy and/or a small side effect by evaluating the degree of inhibition of a target in a whole body and in real time which is impracticable by any prior art technique.

DISCLOSURE OF THE INVENTION

Most of medicines exert the pharmacological effects by inhibiting or enhancing the function of their targets (e.g., bioenzymes or receptors). For example, a medicine containing an enzyme exerts the pharmacological effect by enhancing an in vivo enzymatic reaction, a medicine containing an enzyme inhibitor exerts the pharmacological effect by inhibiting an in vivo enzymatic reaction, and a medicine containing a receptor ligand exerts the pharmacological effect by enhancing or inhibiting the function of a receptor by binding to the receptor, thus by enhancing or inhibiting a related in vivo enzymatic reaction. Accordingly, the pharmacological effect of a medicine can be evaluated by determining the degree of enhancement or inhibition of the function of a target for the medicine upon the administration of the medicine.

The present invention provides a diagnostic reagent for evaluating the pharmacological effect of a medicine which contains a pharmaceutical agent comprising an enzyme, an enzyme inhibitor or a receptor ligand or a prodrug of the pharmaceutical agent, the diagnostic reagent comprising any one of the following substances (a) to (f):

(a) a compound which serves as a substrate for the enzyme contained in the medicine to be evaluated or for an enzyme generated from the prodrug contained in the medicine to be evaluated, or a pharmaceutically acceptable salt thereof;

(b) a compound which serves as a substrate for a different enzyme capable of exhibiting an alteration in activity by coupling to the effect of the enzyme contained in the medicine to be evaluated or the effect of an enzyme generated from the prodrug contained in the medicine to be evaluated, or a pharmaceutically acceptable salt thereof;

(c) a compound which serves as a substrate for an enzyme which is directly inhibited by the enzyme inhibitor contained in the medicine to be evaluated or by an enzyme inhibitor generated from the prodrug contained in the medicine to be evaluated, or a pharmaceutically acceptable salt thereof;

(d) a compound which serves as a substrate for an enzyme capable of exhibiting an alteration in activity by coupling to the effect of the enzyme inhibitor for the other enzyme, contained in the medicine to be evaluated or the effect of an enzyme inhibitor generated from the prodrug contained in the medicine to be evaluated, or a pharmaceutically acceptable salt thereof;

(e) a compound which serves as a substrate for an enzyme capable of exhibiting an alteration in activity by the binding between a receptor and the receptor ligand contained in the medicine to be evaluated or a receptor ligand generated from the prodrug contained in the medicine to be evaluated, or a pharmaceutically acceptable salt thereof; or (f) a labeled form of any one of the substances (a) to (e).

The diagnostic reagent of the present invention may be used in a method of evaluating the pharmacological effect of a medicine, the method comprising the steps of:

administering to a subject the medicine and the diagnostic reagent comprising any one of the following substances (a) to (f):

(a) a compound which serves as a substrate for an enzyme contained in the medicine to be evaluated or for an enzyme generated from a prodrug contained in the medicine to be evaluated, or a pharmaceutically acceptable salt thereof;

(b) a compound which serves as a substrate for a different enzyme capable of exhibiting an alteration in activity by coupling to the effect of an enzyme contained in the medicine to be evaluated or the effect of an enzyme generated from a prodrug contained in the medicine to be evaluated, or a pharmaceutically acceptable salt thereof;

(c) a compound which serves as a substrate for an enzyme which is directly inhibited by an enzyme inhibitor contained in the medicine to be evaluated or by an enzyme inhibitor generated from a prodrug contained in the medicine to be evaluated, or a pharmaceutically acceptable salt thereof;

(d) a compound which serves as a substrate for an enzyme capable of exhibiting an alteration in activity by coupling to the effect of an enzyme inhibitor for the other enzyme, contained in the medicine to be evaluated or the effect of an enzyme inhibitor generated from a prodrug contained in the medicine to be evaluated, or a pharmaceutically acceptable salt thereof;

(e) a compound which serves as a substrate for an enzyme capable of exhibiting an alteration in activity by the binding between a receptor and a receptor ligand contained in the medicine to be evaluated or a receptor ligand generated from a prodrug contained in the medicine to be evaluated, or a pharmaceutically acceptable salt thereof; or (f) a labeled form of any one of the substances (a) to (e);

collecting a biological sample from the subject at least once;

measuring the amount of the substance or a metabolite thereof in the biological sample; and evaluating the pharmacological effect of the medicine based on the value obtained in the measurement step.

The medicine may be administered to the subject once or more times concurrently with or before the administration of the diagnostic reagent of the present invention.

In the method above, in the case where the diagnostic reagent comprises a $^{13}C$-labeled form of any one of the substances (a) to (e), the $^{13}C$ level in exhaled $CO_2$ in the subject may be measured.

As used herein, the term "medicine containing an enzyme" refers to a pharmaceutical preparation which can produce the pharmaceutical efficacy by enhancing an in vivo enzymatic reaction upon the administration of the enzyme. Examples of the medicine containing an enzyme include those preparations each containing streptokinase, streptodornase, hyaluronidase, urokinase, lysozyme, amylase, saccharated pepsin, diastase, pancreatin or the like.

The term "enzyme inhibitor" refers to a substance which can bind to a bioenzyme (i.e., an enzyme in a living body) to delay or stop the reaction rate (see "Yakubutsu Taisha Jiten" (Dictionary of Drug Metabolisms), edited by Ikuo Yamamoto, (1996) p.241). Examples of the enzyme inhibitor include acarbose (α-glucosidase inhibitor) which is used as an anti-diabetes agent; a HMG-CoA reductase inhibitor such as simvastatin, atorvastatin, pravastatin, fluvastatin and cerivastatin which are used as anti-hyperlipidemia agents; an angiotensin converting enzyme inhibitor such as enalapril maleate, alacepril, imidapril hydrochloride, quinapril hydrochloride, captopril and cilazapril which are used as anti-hypertensive agents; methotrexate (folate reductase inhibitor) and fadrozole hydrochloride (aromatase inhibitor) which are used as anti-neoplastic agents; an HIV protease inhibitor such as saquinavir mesylate, zidovudine (a viral reverse transcriptase inhibitor); foscarnet (DNA polymerase inhibitor) which are used as anti-AIDS agents; and a neuraminidase inhibitor such as zanamivir hydrate which is used as an anti-influenza agent.

The term "receptor ligand" refers to a substance which can specifically bind to a receptor protein on the cell membrane or in a cell. Upon the binding of a receptor ligand to a receptor, a biological reaction specific to the combination of the receptor and the receptor ligand occurs. Receptor ligands which naturally occur in a living body include a hormone, a neurotransmitter and the like. In the case where the receptor ligand naturally occurring in a living body is administered as a pharmaceutical agent, it is used as a stimulant or agonist for enhancing a biological reaction caused by the binding of the receptor ligand to its receptor. Alternatively, the receptor ligand may also be used as an antagonist or blocker for inhibiting or blocking such a biological reaction. Specific examples of the receptor ligand include histamine $H_2$ receptor blockers including ranitidine hydrochloride, cimetidine, famotidine and lafutidine which are used as therapeutic agents for peptic ulcer; hormonal agents including estradiol and derivatives thereof, estriol and derivatives thereof, progesterone and derivatives thereof and testosterone and derivatives thereof; α-receptor inhibitors including tolazoline, ifenprodil and nicergoline which are used as vasodilators; and β-receptor blockers including alprenolol hydrochloride and bufetolol hydrochloride which are used as therapeutic agents for angina pectoris.

The term "prodrug" refers to a substance which is pharmacologically inactive in nature but can be converted into a substance having a pharmacological effect by an enzymatic or non-enzymatic reaction in vivo (see "Yakubutsu Taisha Jiten" (the Dictionary of Drug Metabolisms), edited by Ikuo Yamamoto, (1996) p.377). Examples of the prodrug include sulindac which can be converted by reduction into a sulfide form having antiphlogistic and analgesic effects; loxoprofen which can be converted into a trans-OH form having antiphlogistic and analgesic effects; nabumetone which can be converted into 6-methoxy-2-naphtylacetic acid having antiphlogistic and analgesic effects; and indomethacinfarnesyl which can be converted into indomethacin having antiphlogistic and analgesic effects.

The term "pharmacological effect of a medicine" refers to an effect which is produced by enhancing or inhibiting the function of a target (a bioenzyme or receptor), including medicative efficacy and a side effect. Medicative efficacy means an improvement in pathologic state produced by prolonged enhancement or inhibition of the function of a target (a bioenzyme or receptor), and a side effect means a harmful effect produced by such prolonged enhancement or inhibition.

Accordingly, the "evaluation of a pharmacological effect of a medicine" refers to the evaluation of whether an enhancement or inhibition of the function of a target for a medicine is achieved sufficiently to improve the pathologic state, or the evaluation of whether an enhancement or inhibition of the function of a target for a medicine which may produce a side effect is caused.

The term "substrate for an enzyme" refers to a substance which can undergo a change by directly binding to the enzyme. Examples of the enzyme and its substrate include diastase and cyclodextrin; α-glucosidase and maltose; pancreatin and a protein; HMG-CoA reductase and HMG-CoA; and aromatase and androgen.

The term "different enzyme capable of exhibiting an alteration in activity by coupling to the effect of an enzyme" refers to a different enzyme which can constitute a coupling reaction system with the enzyme, a different enzyme which can be activated by the enzyme, or the like.

Examples of the enzyme, the different enzyme capable of exhibiting an alteration in activity by coupling to the effect of the enzyme and the substrate for the different enzyme are those shown in the table below.

TABLE 1

| (1) Enzymes | (2) Different enzymes capable of exhibiting an alteration in activity by coupling to the effect of (1) | (3) Substrates for (2) |
| --- | --- | --- |
| Enterokinase | Trypsin | Peptide |
| Trypsin | Carboxypeptidase A | Peptide |

The term "enzyme capable of exhibiting an alteration in activity by coupling to the effect of an enzyme inhibitor for the other enzyme," refers to an enzyme which can constitute a coupling reaction system with the other enzyme that is directly inhibited by the enzyme inhibitor so that the enzyme itself is not inhibited by the enzyme inhibitor but causes the alteration in its activity, or the like.

Examples of the enzyme inhibitor, the enzyme which is directly inhibited by the enzyme inhibitor and its substrate, and the enzyme capable of exhibiting an alteration in activity by coupling to the effect of the enzyme inhibitor and its substrate are those shown in the table below.

TABLE 2

| (1) Enzyme inhibitors | (2) Enzymes directly inhibited by (1) | (3) Substrates for (2) | (4) Enzymes capable of exhibiting an alteration in activity by coupling to the effect of (1) but is not directly inhibited by (1) | (5) Substrates for (4) |
| --- | --- | --- | --- | --- |
| Methotrexate | Folate reductase | Folate | Thymidylate synthase | dUMP |
| Ozagrel sodium | Thromboxane synthetase | Prostaglandin I$_2$ | Prostaglandin I synthetase | Prostaglandin H$_2$ |

Examples of the enzyme capable of exhibiting an alteration in activity by the binding of a ligand to a receptor and the substrate for the enzyme include are those shown in the table below.

TABLE 3

| (1) Receptors | (2) Ligands for (1) | (3) Enzymes capable of exhibiting an alteration in activity by binding between (1) and (2) | (4) Substrates for (3) |
| --- | --- | --- | --- |
| Dopamine receptor | Bromocriptine, cabergoline | Adenylate cyclase | ATP |
| Acetylcholine receptor | Acetylcholine chloride, bethanechol chloride | Adenylate cyclase | ATP |
| Adrenergic receptor | Norepinephrine, isoproterenol, phentolamine | Adenylate cyclase | ATP |

The term "labeled form" means a state where a compound or its metabolite has a detectable property. Examples of the labeling method include those methods using an isotope such as a stable isotope (e.g., $^{13}C$, $^{15}N$, $^{2}H$ and $^{18}O$) and a radioactive isotope (e.g., $^{14}C$, $^{3}H$, $^{35}S$, $^{32}P$ and $^{125}I$), a luminescent or fluorescent substituent (e.g., fluorescein, methylcoumarylamide, calcein and rhodamine), or the like.

The term "$^{13}C$-labeled form" refers to a substance having an increased $^{13}C$ level compared with the natural abundance. Particularly, a substance having an increased $^{13}C$ level at a specific position is desirable. Examples of the $^{13}C$-labeled form include, but are not limited to, organic acids such as commercially available $^{13}C$-labeled $NaHCO_3$, $^{13}C$-labeled formic acid, $^{13}C$-labeled acetic acid, $^{13}C$-labeled propionic acid, $^{13}C$-labeled lactic acid, $^{13}C$-labeled butyric acid, $^{13}C$-labeled pyruvic acid and $^{13}C$-labeled benzoic acid; $^{13}C$-labeled amino acids such as $^{13}C$-labeled alanine; $^{13}C$-labeled saccharides such as $^{13}C$-labeled glucose; and $^{13}C$-labeled alcohols such as $^{13}C$-labeled ethanol.

The term "subject" refers to a living body to be administered with the diagnostic reagent of the present invention, wherein the "living body" means a living individual organism. Examples of the subject include: (1) human; (2) domestic animals such as dogs and cats; (3) laboratory animals such as rats, mice, guinea pigs, rabbits and monkeys; or (4) other mammals.

The biological sample to be collected from the subject is, for example, breath, blood or urine.

The term "metabolite" refers to a substance which is produced in the metabolism process of a substance that is administered to a living organism. Examples of the metabolites of the substances (a) to (f) above are those substances shown in the table below.

TABLE 4

| (1) Substances corresponding to (a) to (e) | (2) Medicines to be evaluated by the diagnostic reagents (1) | (3) Metabolites of (1) |
|---|---|---|
| Maltose | Acarbose | Glucose, $CO_2$ |
| Mevaltic CoA hemiacetal | HMG-CoA reductase inhibitor | Mevalonic acid, $CO_2$ |
| Androgen | Aromatase inhibitor | Estrogen |
| dUMP | Methotrexate | dTMP |

Most of medicines exert the pharmacological effects by enhancing or inhibiting the function of their targets (e.g., bioenzymes or receptors). For example, a medicine containing an enzyme exerts the pharmacological effect by enhancing an in vivo enzymatic reaction, a medicine containing an enzyme inhibitor exerts the pharmacological effect by inhibiting an in vivo enzymatic reaction, and a medicine containing a receptor ligand exerts the pharmacological effect by enhancing or inhibiting the function of a receptor by binding to the receptor, thus by enhancing or inhibiting a related in vivo enzymatic reaction. Accordingly, the pharmacological effect of a medicine can be evaluated by determining the degree of enhancement or inhibition of the function of a target for the medicine upon the administration of the medicine. The diagnostic reagent of the present invention is one for evaluating the pharmacological effect of a medicine by determining the degree of enhancement or inhibition of the function of a target.

The principle of the evaluation method is as follows.

1. A case where the target is an enzyme (for a medicine containing an enzyme, an enzyme inhibitor or a prodrug thereof)

The degree of enhancement or inhibition of the function of a target by a medicine is evaluated by administering to a subject a substrate for the target, a substrate for a second enzyme involved in an enzymatic reaction that can undergo a change by the enhancement or inhibition of the function of the target (e.g., a coupling reaction with the target) or a labeled form of either substrate as a diagnostic reagent, and then determining the increase or decrease in the amount of a metabolite derived from the diagnostic reagent or the diagnostic reagent per se caused by the enhancement or inhibition of the function of the target. For example, in the case of a medicine containing an enzyme, a substrate for a bioenzyme (a target for the medicine) or a labeled form of the substrate is administered to a subject as a diagnostic reagent. If the amount of a metabolite derived from the diagnostic reagent is increased after the administration, then the medicine would be considered to enhance the function of the target. Thus, it can be confirmed that the medicine has a sufficient efficacy. In the case of a medicine containing an enzyme inhibitor, for example, a substrate for an enzyme (a target for the medicine) or a labeled form of the substrate is administered to a subject as a diagnostic reagent. If little metabolite derived from the diagnostic reagent is detected, then the medicine would be considered to inhibit the function of the target satisfactorily. Thus, it can be confirmed that the medicine has sufficient medicative efficacy.

2. A case where the target is a receptor (for a medicine containing a receptor ligand or a prodrug thereof)

The degree of enhancement or inhibition of the function of a target by a medicine is evaluated by administering to a subject a substrate for an enzymatic reaction that can undergo a change by the binding of the medicine to the target or a labeled form of the substrate as a diagnostic reagent, and then determining the increase or decrease in the amount of a metabolite derived from the diagnostic reagent or the diagnostic reagent per se caused by the enzymatic reaction. For example, in the case where a substrate for an in vivo enzymatic reaction that can be enhanced by the binding of the medicine to the target or a labeled form of the substrate is administered to a subject as a diagnostic reagent, if the amount of a metabolite derived from the diagnostic reagent is increased, then the medicine would be considered to enhance the function of the target. Thus, it can be confirmed that the medicine has a sufficient efficiency. In the case where a substrate for an in vivo enzymatic reaction which can be inhibited by the binding of the medicine to the target or a labeled form of the substrate is administered to a subject as a diagnostic reagent, for example, if little metabolite derived from the diagnostic reagent is detected, then the medicine would be considered to inhibit the function of the target completely. Thus, it can be confirmed that the medicine has sufficient medicative efficacy.

The diagnostic reagent of the present invention may be formulated into an oral preparation (e.g., tablet, capsule, powder, granule, solution) or an injectable preparation depending on the route of administration, using any one of the following substances (a) to (f) alone or in combination with an excipient or carrier:

(a) a compound which serves as a substrate for the enzyme contained in the medicine to be evaluated or for an enzyme generated from the prodrug contained in the medicine to be evaluated, or a pharmaceutically acceptable salt thereof;

(b) a compound which serves as a substrate for a different enzyme capable of exhibiting an alteration in activity by coupling to the effect of the enzyme contained in the medicine to be evaluated or the effect of an enzyme generated from the prodrug contained in the medicine to be evaluated, or a pharmaceutically acceptable salt thereof;

(c) a compound which serves as a substrate for an enzyme which is directly inhibited by the enzyme inhibitor contained in the medicine to be evaluated or by an enzyme inhibitor generated from the prodrug contained in the medicine to be evaluated, or a pharmaceutically acceptable salt thereof;

(d) a compound which serves as a substrate for an enzyme capable of exhibiting an alteration in activity by coupling to the effect of the enzyme inhibitor for the other enzyme, contained in the medicine to be evaluated or the effect of an enzyme inhibitor generated from the prodrug contained in the medicine to be evaluated, or a pharmaceutically acceptable salt thereof;

(e) a compound which serves as a substrate for an enzyme capable of exhibiting an alteration in activity by the binding between a receptor and the receptor ligand contained in the medicine to be evaluated or a receptor ligand generated from the prodrug contained in the medicine to be evaluated, or a pharmaceutically acceptable salt thereof; or (f) a labeled form of any one of the substances (a) to (e).

With respect to the substances (a) to (f), examples of the pharmaceutically acceptable salt include salts with inorganic acids such as hydrochloric acid, sulfuric acid, nitric acid and phosphoric acid; salts with organic acids such as acetic acid, propionic acid, succinic acid, malic acid, tartaric acid, citric acid and maleic acid; salts with alkali metals such as sodium and potassium; and salts with alkaline earth metals such as calcium.

The substances (a) to (f) may be commercially available products or may be produced from commercially available raw materials according to known methods.

For example, $^{13}$C-labeled DOPA can be produced as described in Production Example 1 below. In the same manner, $^{14}$C-labeled DOPA may also be produced.

A $^{13}$C- or $^{14}$C-labeled peptide or a salt thereof can be synthesized using a commercially available $^{13}$C- or $^{14}$C-labeled amino acid according to known methods, for example according to the method described in "Jikkenkagakukouza 22" (volume 22 of A Course in Experimental Chemistry), Organic Synthesis IV, edited by the Chemical Society of Japan, published by Maruzen (1992). An example of the production method is illustrated below.

A $^{13}$C-labeled amino acid is dissolved in hydrogen chloride/methanol and then refluxed. The resulting methyl ester is suspended in dichloromethane, and triethylamine is then added dropwise thereto while stirring under ice-cooling. To the solution are added N-benzoyl-amino acid, HOBt (1-hydroxy-1H-benzotriazole.H$_2$O) and dichloromethane. A solution of WSC (1-ethyl-3-(3-dimethylaminopropyl)-carbodiimide.HCl) in dichloromethane is added to the mixed solution and then stirred. After concentration, the solution is extracted with ethyl acetate, washed with in hydrochloric acid, 5% NaHCO$_3$ and water, dried over magnesium sulfate, concentrated to dryness and then optionally saponified, thereby yielding a $^{13}$C-labeled peptide.

A $^{13}$C- or $^{14}$C-labeled oligosaccharide or polysaccharide or a salt thereof can be synthesized according to any method described in the literature (Carbohydrate Research, 176(1988), 107-115; Japanese Patent Application Publication No. 3-91496; U.S. Pat. No. 4,649,108; Journal of Chromatography, 336(1984), 368-373; Japanese Patent Application Publication No. 8-291). In this case, $^{13}$C- or $^{14}$C-labeled forms of the compounds above can be synthesized starting from, for example, a commercially available $^{13}$C- or $^{14}$C-labeled maltooligosaccharide or a $^{13}$C- or $^{14}$C-labeled maltooligosaccharide produced by known methods.

For example, galactosyloligosaccharide, which is one of oligosaccharides having a modified non-reducing terminus, can be produced by adding lactose to an oligosaccharide, treating the resulting mixture with lactase and separating the desired product from the reaction mixture by column chromatography (Japanese Patent Application Publication Nos. 4-209277, 8-196289 and 10-316697). In this case, $^{13}$C- or $^{14}$C-labeled galactosyloligosaccharide can be produced by using a $^{13}$C- or $^{14}$C-labeled oligosaccharide, and galactosyloligosaccharide having a $^{13}$C- or $^{14}$C-labeled galactosyl group can be produced by using a $^{13}$C- or $^{14}$C-galactosyl-labeled lactic acid, for example.

The excipient or carrier may be any one which is conventionally used in the art and is pharmaceutically acceptable. The type and the composition of the excipient or carrier may be varied appropriately depending on the route and method of administration. For example, water can be used as a liquid carrier. As a solid carrier, a cellulose derivative such as hydroxypropyl cellulose, a salt with an organic acid such as magnesium stearate can be used. For an injectable preparation, sterile water, physiological saline and various types of buffers are generally preferred. A lyophilized preparation may also be possible, which can be used as an oral preparation or can be administered by dissolving in a proper solvent for injection such as a solution for intravenous administration (e.g., sterile water, physiological saline and an electrolyte solution) before use.

The content of any one of the substances (a) to (f) above (hereinafter, referred to as "a main ingredient") in the pharmaceutical preparation may vary depending on the type of the pharmaceutical preparation, but is generally 1 to 100% by weight, preferably 50 to 100% by weight. For example, in an injectable preparation, the main ingredient may be generally added in a content of 1 to 40% by weight. In a capsule, tablet, granule or powder preparation, the content of the main ingredient in the preparation is about 10 to 100% by weight, preferably 50 to 100% by weight, with the remainder being a carrier.

The dose amount of the diagnostic reagent of the present invention should be an amount sufficient to enable the detection of the main ingredient or its metabolite in a biological sample from a subject, and may vary depending on the age and body weight of the subject and the intended purpose of the test. For example, the unit dose amount is about 1 to 1000 mg/kg body weight for an adult human.

In the test with the diagnostic reagent of the present invention, the diagnostic reagent of the present invention may be administered (e.g., orally) to a subject after or concurrently with the administration (e.g., oral) of a medicine. The amount of migration into the blood or the amount of excretion out of the body (e.g., the amount of excretion into the urine or breath) after a predetermined time period, or the integral or time course (onset slope, change in slope, peak time, etc.) of the amount of migration into the blood or the amount of excretion out of the body during a predetermined time period after the administration is measured with respect to the main ingredient or its metabolite. Based on the measurement date, the pharmacological effect of the medicine can be determined.

The method for the measurement is properly selected depending on the nature or type of the material to be tested (e.g., blood, urine, breath) and the substance to be administered (main ingredient), and includes colorimetry, fluorometry, mass spectrometry, NMR (nuclear magnetic resonance), HPLC, gas chromatography, gas chromatography-mass spectrometry (GC-MS), photoelectric acoustic spectroscopy, GM counter method, liquid scintillation, solid scintillation, autoradiography, ionization chamber method and the like.

Specifically, for determining the amount of migration into the blood, the removed blood may be used for measurement without any treatment or may be subjected to some treatment (e.g., isolation, pretreatment) before measurement. For example, the determination can be carried out by administering a compound labeled with a fluorescent residue as a diagnostic reagent, removing the blood after a predetermined time period, preparing the serum or plasma from the blood, and then comparing the fluorescence intensity in the serum or plasma. In the case where a compound labeled with a substituent having an absorption somewhere in the ultraviolet or visible region is administered as a diagnostic reagent, the determination can be carried out by removing the blood after a predetermined time period, and then measuring the absorption in the ultraviolet or visible region of a serum or plasma sample from the blood with an absorptiometer or the like. Alternatively, the absorption in the ultraviolet or visible region of the blood may be measured externally on the skin without removing the blood.

In the case where the urine is used as a sample, the removed urine may be used for measurement without any treatment or may be subjected to some treatment (e.g., isolation, pretreatment) before measurement. For example, the determination can be carried out by administering a compound labeled with a fluorescent residue as a diagnostic reagent, removing the urine after a predetermined time period, and then comparing the fluorescence intensity in the urine. In the case where a compound labeled with a substituent having an absorption somewhere in the ultraviolet or visible region is administered as a diagnostic reagent, the determination can be carried out by removing the urine after a predetermined time period, and measuring the absorption in the ultraviolet or visible region of the urine with an absorptiometer or the like.

For determining the amount of excretion in the breath using, for example, a $^{13}C$-labeled compound as a diagnostic reagent, the determination can be carried out by gas chromatography-mass spectrometry (GC-MS), infrared spectroscopy, mass spectroscopy, photoelectric acoustic spectroscopy, NMR (nuclear magnetic resonance) or the like on $^{13}CO_2$. In the case where a $^{14}C$-labeled compound is used as a diagnostic reagent, the breath, either without any treatment or after trapping $CO_2$ in a solvent, can be subjected to measurement with a GM counter, a liquid scintillation counter or a solid scintillation counter or by autoradiography, ionization chamber method or the like.

As stated above, most of medicines exert the pharmacological effects by enhancing or inhibiting the function of their targets (bioenzymes or receptors). For example, a pharmaceutical agent comprising an enzyme can exert the pharmacological effect by enhancing an in vivo enzymatic reaction, a pharmaceutical agent comprising an enzyme inhibitor or a prodrug of the pharmaceutical agent can exert the pharmacological effect by inhibiting an in vivo enzymatic reaction, and a pharmaceutical agent comprising a receptor ligand or a prodrug of the pharmaceutical agent can exert the pharmacological effect by enhancing or inhibiting the function of a receptor by the binding of the ligand to the receptor, thus by enhancing or inhibiting a related in vivo enzymatic reaction. Accordingly, the pharmacological effect of a medicine can be evaluated by determining the degree of enhancement or inhibition of a function of a target for a pharmaceutical agent or its prodrug upon the administration of the pharmaceutical agent or prodrug. By applying this principle, it becomes possible to screen for high medicative efficacy and/or a small side effect among pharmaceutical agents and/or prodrugs thereof.

The present invention provides a method of screening pharmaceutical agents each comprising an enzyme, an enzyme inhibitor or a receptor ligand and/or prodrugs of the pharmaceutical agents for one or ones having high medicative efficacy and/or a small side effect, the method comprising the steps of:

selecting a pharmaceutical agent or prodrug to be evaluated from pharmaceutical agents each comprising an enzyme, an enzyme inhibitor or a receptor ligand and/or prodrugs of the pharmaceutical agents;

administering to a non-human subject the pharmaceutical agent or prodrug to be evaluated and a reagent comprising any one of the following substances (a) to (f):

(a) a compound which serves as a substrate for the enzyme which is included in the pharmaceutical agent to be evaluated or for an enzyme generated from the prodrug to be evaluated, or a pharmaceutically acceptable salt thereof;

(b) a compound which serves as a substrate for a different enzyme capable of exhibiting an alteration in activity by coupling to the effect of the enzyme which is included in the pharmaceutical agent to be evaluated or the effect of an enzyme generated from the prodrug to be evaluated, or a pharmaceutically acceptable salt thereof;

(c) a compound which serves as a substrate for an enzyme which is directly inhibited by the enzyme inhibitor which is included in the pharmaceutical agent to be evaluated or by an enzyme inhibitor generated from the prodrug to be evaluated, or a pharmaceutically acceptable salt thereof;

(d) a compound which serves as a substrate for an enzyme capable of exhibiting an alteration in activity by coupling to the effect of the enzyme inhibitor for the other enzyme, which is included in the pharmaceutical agent to be evaluated or the effect of an enzyme inhibitor generated from the prodrug to be evaluated, or a pharmaceutically acceptable salt thereof;

(e) a compound which serves as a substrate for an enzyme capable of exhibiting an alteration in activity by the binding between a receptor and the receptor ligand which is included in the pharmaceutical agent to be evaluated or a receptor ligand generated from the prodrug to be evaluated, or a pharmaceutically acceptable salt thereof; or (f) a labeled form of any one of the substances (a) to (e);

collecting a biological sample from the subject at least once;

measuring the amount of the any one of the substances (a) to (f) above or a metabolite thereof in the biological sample; and evaluating the pharmacological effect of the pharmaceutical agent or prodrug to be evaluated based on the value obtained in the measurement step. The pharmaceutical agent and/or prodrug to be screened according to this method preferably has as higher medicative efficacy, as smaller a side effect, or as higher medicative efficacy and as smaller a side effect, as possible.

The pharmaceutical agent and/or prodrug to be evaluated may be administered to the subject once or more times concurrently with or before the administration of the reagent comprising any one of the substances (a) to (f).

The present invention also provides a reagent for use in the screening pharmaceutical agents each comprising an enzyme, an enzyme inhibitor or a receptor ligand and/or prodrugs of the pharmaceutical agents for one or ones having high medicative efficacy and/or a small side effect, the reagent comprising any one of the following substances (a) to (f):

(a) a compound which serves as a substrate for the enzyme which is included in the pharmaceutical agent to be evaluated or for an enzyme generated from the prodrug to be evaluated, or a pharmaceutically acceptable salt thereof;

(b) a compound which serves as a substrate for a different enzyme capable of exhibiting an alteration in activity by coupling to the effect of the enzyme which is included in the pharmaceutical agent to be evaluated or the effect of an enzyme generated from the prodrug to be evaluated, or a pharmaceutically acceptable salt thereof;

(c) a compound which serves as a substrate for an enzyme which is directly inhibited by the enzyme inhibitor which is included in the pharmaceutical agent to be evaluated or by an enzyme inhibitor generated from the prodrug to be evaluated, or a pharmaceutically acceptable salt thereof;

(d) a compound which serves as a substrate for an enzyme capable of exhibiting an alteration in activity by coupling to the effect of the enzyme inhibitor for the other enzyme, which is included in the pharmaceutical agent to be evaluated or the effect of an enzyme inhibitor generated from the prodrug to be evaluated, or a pharmaceutically acceptable salt thereof;

(e) a compound which serves as a substrate for an enzyme capable of exhibiting an alteration in activity by the binding between a receptor and the receptor ligand which is included in the pharmaceutical agent to be evaluated or a receptor ligand generated from the prodrug to be evaluated, or a pharmaceutically acceptable salt thereof; or (f) a labeled form of any one of the substances (a) to (e).

The reagent of the present invention may be used in the method of screening pharmaceutical agents each comprising an enzyme, an enzyme inhibitor or a receptor ligand and/or prodrugs of the pharmaceutical agents for one or ones having high medicative efficacy and/or a small side effect, the method comprising the steps of:

selecting a pharmaceutical agent or prodrug to be evaluated from pharmaceutical agents each comprising an enzyme, an enzyme inhibitor or a receptor ligand and/or prodrugs of the pharmaceutical agents;

administering to a non-human subject the pharmaceutical agent or prodrug to be evaluated and a reagent comprising any one of the following substances (a) to (f):

(a) a compound which serves as a substrate for the enzyme which is included in the pharmaceutical agent to be evaluated or for an enzyme generated from the prodrug to be evaluated, or a pharmaceutically acceptable salt thereof;

(b) a compound which serves as a substrate for a different enzyme capable of exhibiting an alteration in activity by coupling to the effect of the enzyme which is included in the pharmaceutical agent to be evaluated or the effect of an enzyme generated from the prodrug to be evaluated, or a pharmaceutically acceptable salt thereof;

(c) a compound which serves as a substrate for an enzyme which is directly inhibited by the enzyme inhibitor which is included in the pharmaceutical agent to be evaluated or by an enzyme inhibitor generated from the prodrug to be evaluated, or a pharmaceutically acceptable salt thereof;

(d) a compound which serves as a substrate for an enzyme capable of exhibiting an alteration in activity by coupling to the effect of the enzyme inhibitor for the other enzyme, which is included in the pharmaceutical agent to be evaluated or the effect of an enzyme inhibitor generated from the prodrug to be evaluated, or a pharmaceutically acceptable salt thereof;

(e) a compound which serves as a substrate for an enzyme capable of exhibiting an alteration in activity by the binding between a receptor and the receptor ligand which is included in the pharmaceutical agent to be evaluated or a receptor ligand generated from the prodrug to be evaluated, or a pharmaceutically acceptable salt thereof; or (f) a labeled form of any one of the substances (a) to (e);

collecting a biological sample from the subject at least once;

measuring the amount of the any one of the substances (a) to (f) or a metabolite thereof in the biological sample; and evaluating the pharmacological effect of the pharmaceutical agent or prodrug to be evaluated based on the value obtained in the measurement step. The pharmaceutical agent and/or prodrug to be screened according to this method preferably has as higher medicative efficacy, as smaller a side effect, or as higher medicative efficacy and as smaller a side effect, as possible.

The pharmaceutical agent and/or prodrug to be evaluated may be administered to the subject once or more times concurrently with or before the administration of the reagent of the present invention.

In the screening method and the reagent of the present invention, in the case where the reagent comprises a $^{13}$C-labeled form of any one of the substances (a) to (e), the $^{13}$C level in exhaled $CO_2$ of the subject may be measured.

In the present specification, the term "pharmaceutical agent comprising an enzyme" refers to a pharmaceutical preparation which can exert the pharmacological effect by enhancing an in vivo enzymatic reaction upon the administration of the enzyme. Examples of the pharmaceutical agent comprising an enzyme include those preparations each comprising streptokinase, streptodornase, hyaluronidase, urokinase, lysozyme, amylase, saccharated pepsin, diastase, pancreatin or the like.

The term "enzyme inhibitor" is as defined above.

The term "receptor ligand" is as defined above.

The term "prodrug" is as defined above.

The term "pharmacological effect of a pharmaceutical agent or a prodrug thereof" refers to an effect which is produced by enhancing or inhibiting the function of a target (a bioenzyme or receptor), including medicative efficacy and a side effect. Medicative efficacy means an improvement in pathologic state produced by the prolonged enhancement or inhibition of the function of a target (a bioenzyme or receptor), and a side effect means a harmful effect produced by such prolonged enhancement or inhibition.

Accordingly, "evaluation of a pharmacological effect of a pharmaceutical agent or a prodrug thereof" refers to the evaluation of whether the enhancement or inhibition of the function of a target for the pharmaceutical agent or prodrug is achieved sufficiently to improve a pathologic state, or the evaluation of whether the enhancement or inhibition of the function of a target for a medicine which may produce a side effect is prevented.

The term "substrate for an enzyme" is as defined above.

The "different enzyme capable of exhibiting an alteration in activity by coupling to the effect of an enzyme" is as defined above.

Examples of the enzyme, the different enzyme capable of exhibiting an alteration in activity by coupling to the effect of the enzyme and the substrate for the different enzyme are those shown Table 1 above.

The term "enzyme capable of exhibiting an alteration in activity by coupling to the effect of an enzyme inhibitor" is as defined above.

Examples of the enzyme inhibitor, the enzyme directly inhibited by the enzyme inhibitor and its substrate, and the enzyme capable of exhibiting an alteration in activity by coupling to the effect of the enzyme inhibitor and its substrate are those shown in Table 2 above.

Examples of the enzyme capable of exhibiting an alteration in activity by the binding of the ligand to the receptor and the substrate for the enzyme are those shown in Table 3 above.

The term "labeled form" is as defined above.

The term "$^{13}$C-labeled form" is as defined above.

The term "subject" is as defined above.

The term "metabolite" refers to a substance which is produced in the metabolism process of a substance that is administered to a living organism. Examples of the metabolites of the substances (a) to (f) above include those substances shown in Table 5 below.

TABLE 5

| (1) Substances corresponding to (a) to (e) | (2) Pharmaceutical agents screened with (1) | (3) Metabolites of (1) |
| --- | --- | --- |
| Maltose | Acarbose | Glucose, $CO_2$ |
| Mevaltic CoA hemiacetal | HMG-CoA reductase inhibitor | Mevalonic acid, $CO_2$ |
| Androgen | Aromatase inhibitor | Estrogen |
| dUMP | Methotrexate | dTMP |

Most of pharmaceutical agents and their prodrugs produce the pharmacological effects by enhancing or inhibiting the function of their targets (bioenzymes or receptors). For example, a pharmaceutical agent comprising an enzyme can exhibit the pharmacological effect by enhancing an in vivo enzymatic reaction, a pharmaceutical agent comprising an enzyme inhibitor or an enzyme inhibitor generated from a prodrug can exhibit the pharmacological effect by inhibiting an in vivo enzymatic reaction, and a pharmaceutical agent comprising a receptor ligand or a receptor ligand generated from a prodrug can exhibit the pharmacological effect by enhancing or inhibiting the function of a receptor by binding to the receptor, thus by enhancing or inhibiting a related in vivo enzymatic reaction. Accordingly, the pharmacological effect of a pharmaceutical agent can be evaluated by determining the degree of enhancement or inhibition of the function of a target for the pharmaceutical agent or its prodrug upon the administration of the pharmaceutical agent or prodrug. The screening method and the reagent of the present invention are those for the screening pharmaceutical agents and/or prodrugs thereof for one or ones having high medicative efficacy and/or a small side effect by the evaluation of the pharmacological effect of a medicine by determining the degree of enhancement or inhibition of the function of a target.

The principle of the evaluation methods is as follows.

1. A case where the target is an enzyme (for the evaluation of an enzyme, an enzyme inhibitor or a prodrug thereof)

The degree of enhancement or inhibition of the function of a target for an enzyme, an enzyme inhibitor or a prodrug thereof is evaluated by administering to a subject a substrate for the target, a substrate for a second enzyme involved in an enzymatic reaction that can undergo a change by the enhancement or inhibition of the function of the target (e.g., a coupling reaction with the target) or a labeled form of either substrate as a screening reagent, and then determining the increase or decrease in the amount of a metabolite derived from the diagnostic reagent or the diagnostic reagent per se caused by the enhancement or inhibition of the function of the target. For example, in the case where an enzyme is to be evaluated, a substrate for a bioenzyme (a target) or a labeled form of the substrate is administered to a subject as a screening reagent. If the amount of a metabolite derived from the screening reagent is increased, then the function of the bioenzyme would be considered to be enhanced. Thus, it can be confirmed that the enzyme to be evaluated has sufficient medicative efficacy. In the case where an enzyme inhibitor is to be evaluated, for example, a substrate for an enzyme (a target) or a labeled form of the substrate is administered to a subject as a screening reagent. If little metabolite derived from the screening reagent is detected, then the enzyme inhibitor would be considered to inhibit the function of the target satisfactorily. Thus, it can be confirmed that the enzyme inhibitor has sufficient medicative efficacy.

2. A case where the target is a receptor (for the evaluation of a receptor ligand or a prodrug thereof)

The degree of enhancement or inhibition of the function of a target by a receptor ligand or its prodrug is evaluated by administering to a subject a substrate for an enzymatic reaction that can undergo a change by the binding of the receptor ligand or its prodrug to the target or a labeled form of the substrate as a screening reagent, and then determining the increase or decrease in the amount of a metabolite derived from the screening reagent or the screening reagent per se caused by the enzymatic reaction. For example, in the case where a substrate for an in vivo enzymatic reaction that can be enhanced by the binding of receptor ligand or its prodrug to the target or a labeled form of the substrate is administered to a subject as a screening reagent, if the amount of a metabolite derived from the screening reagent is increased, then the receptor ligand or its prodrug would be considered to enhance the function of the target. Thus, it can be confirmed that the receptor ligand or its prodrug has a sufficient efficacy. In the case where a substrate for an in vivo enzymatic reaction which can be inhibited by the binding of the receptor ligand or its prodrug to the target or a labeled form of the substrate is administered to a subject as a screening reagent, for example, if little metabolite derived from the screening reagent is detected, then the receptor ligand or its prodrug would be considered to inhibit the function of the target completely. Thus, it can be confirmed that the receptor ligand or its prodrug has sufficient medicative efficacy.

The screening reagent of the present invention may be formulated into an oral preparation (e.g., tablet, capsule, powder, granule, solution) or an injectable preparation depending on the route of administration, using any one of the following substances (a) to (f) alone or in combination with an excipient or carrier:

(a) a compound which serves as a substrate for the enzyme which is included in the pharmaceutical agent to be evaluated or for an enzyme generated from the prodrug to be evaluated, or a pharmaceutically acceptable salt thereof;

(b) a compound which serves as a substrate for a different enzyme capable of exhibiting an alteration in activity by coupling to the effect of the enzyme which is included in the pharmaceutical agent to be evaluated or the effect of an enzyme generated from the prodrug to be evaluated, or a pharmaceutically acceptable salt thereof;

(c) a compound which serves as a substrate for an enzyme which is directly inhibited by the enzyme inhibitor which is included in the pharmaceutical agent to be evaluated or by an enzyme inhibitor generated from the prodrug to be evaluated, or a pharmaceutically acceptable salt thereof;

(d) a compound which serves as a substrate for an enzyme capable of exhibiting an alteration in activity by coupling to the effect of the enzyme inhibitor for the other enzyme, which is included in the pharmaceutical agent to be evaluated or the effect of an enzyme inhibitor generated from the prodrug to be evaluated, or a pharmaceutically acceptable salt thereof;

(e) a compound which serves as a substrate for an enzyme capable of exhibiting an alteration in activity by the binding between a receptor and the receptor ligand which is included in the pharmaceutical agent to be evaluated or a receptor ligand generated from the prodrug to be evaluated, or a pharmaceutically acceptable salt thereof; or (f) a labeled form of any one of the substances (a) to (e).

With respect of the substances (a) to (f), examples of the pharmaceutically acceptable salt include salts with inorganic acids such as hydrochloric acid, sulfuric acid, nitric acid and phosphoric acid; salts with organic acids such as acetic acid, propionic acid, succinic acid, malic acid, tartaric acid, citric acid and maleic acid; salts with alkali metals such as sodium and potassium; and salts with alkaline earth metals such as calcium.

The substances (a) to (f) may be commercially available products or may be produced from commercially available raw materials according to known methods. The methods are as described above.

The excipient or carrier may be any one which is conventionally used in the art and is pharmaceutically acceptable. The type and the composition of the excipient or carrier may be varied appropriately depending on the route and method of administration. For example, water can be used as a liquid carrier. As a solid carrier, a cellulose derivative such as hydroxypropyl cellulose, a salt with an organic acid such as magnesium stearate can be used. For an injectable preparation, sterile water, physiological saline and various types of buffers are generally preferred. A lyophilized preparation may also be possible, which can be used as an oral preparation or can be administered by dissolving in a proper solvent for injection such as a solution for intravenous administration (e.g., sterile water, physiological saline and an electrolyte solution) before use.

The content of any one of the substances (a) to (f) above (hereinafter, referred to as "a main ingredient") in the pharmaceutical preparation may vary depending on the type of the pharmaceutical preparation, but is generally 1 to 100% by weight, preferably 50 to 100% by weight. For example, in an injectable preparation, the main ingredient may be generally added in a content of 1 to 40% by weight. In a capsule, tablet, granule or powder preparation, the content of the main ingredient in the preparation is about 10 to 100% by weight, preferably 50 to 100% by weight, with the remainder being a carrier.

The dose amount of the screening reagent of the present invention should be an amount sufficient to enable the detection of the main ingredient or its metabolite in a biological sample from a subject, and may vary depending on the age and body weight of the subject and the intended purpose of the test. For example, the unit dose amount is about 1 to 1000 mg/kg body weight for an adult human.

In the screening with the reagent of the present invention, the reagent of the present invention may be administered (e.g., orally) to a subject after or concurrently with the administration (e.g., oral) of the pharmaceutical agent or its prodrug to be evaluated. The amount of migration into the blood or the amount of excretion out of the body (e.g., the amount of excretion into the urine or breath) after a predetermined time period, or the integral or time course (onset slope, change in slope, peak time, etc.) of the amount of migration into the blood or the amount of excretion out of the body during a predetermined time period after the administration is measured with respect to the main ingredient or its metabolite. The pharmacological effect of the pharmaceutical agent or its prodrug to be evaluated can be determined based on the measurement data.

The method for the measurement is properly selected depending on the nature or type of the material to be tested (e.g., blood, urine, breath) and the substance to be administered (main ingredient), and includes colorimetry, fluorometry, mass spectrometry, NMR (nuclear magnetic resonance), HPLC, gas chromatography, gas chromatography-mass spectrometry (GC-MS), photoelectric acoustic spectroscopy, GM counter method, liquid scintillation, solid scintillation, autoradiography, ionization chamber method and the like.

Specifically, for determining the amount of migration into the blood, the removed blood may be used for measurement without any treatment or may be subjected to some treatment (e.g., isolation, pretreatment) before measurement. For example, the determination can be carried out by administering a compound labeled with a fluorescent residue as a reagent, removing the blood after a predetermined time period, preparing the serum or plasma from the blood, and then comparing the fluorescence intensity in the serum or plasma. In the case where a compound labeled with a substituent having an absorption somewhere in the ultraviolet or visible region is administered as a reagent, the determination can be carried out by removing the blood after a predetermined time period, and then measuring the absorption in the ultraviolet or visible region of a serum or plasma sample from the blood with an absorptiometer or the like. Alternatively, the absorption in the ultraviolet or visible region of the blood may be measured externally on the skin without removing the blood.

In the case where the urine is used as a sample, the removed urine may be used for measured without any treatment or may be subjected to some treatment (e.g., isolation, pretreatment) before measurement. For example, the determination can be carried out by administering a compound labeled with a fluorescent residue as a reagent, removing the urine after a predetermined time period, and then comparing the fluorescence intensity in the urine. In the case where a compound labeled with a substituent having an absorption somewhere in the ultraviolet or visible region is administered as a reagent, the determination can be carried out by removing the urine after a predetermined time period, and measuring the absorption in the ultraviolet or visible region of the urine with a spectrophotometer or the like.

For determining the amount of excretion in the breath using, for example, a $^{13}$C-labeled compound as a reagent, the determination can be carried out by gas chromatography-mass spectrometry (GC-MS), infrared spectroscopy, mass spectroscopy, photoelectric acoustic spectroscopy, NMR (nuclear magnetic resonance) or the like on $^{13}CO_2$. In the case where a $^{14}$C-labeled compound is used as a reagent, the breath, either without any treatment or after trapping $CO_2$ in a solvent, can be subjected to measurement with a GM counter, a liquid scintillation counter or a solid scintillation counter or by autoradiography, ionization chamber method or the like.

This specification includes part or all of the contents as disclosed in the specifications and/or drawings of Japanese Patent Application Nos. 2002-44526 and 2002-44791 which are priority documents of the present application.

BEST MODE FOR CARRYING OUT THE INVENTION

Figure 1:
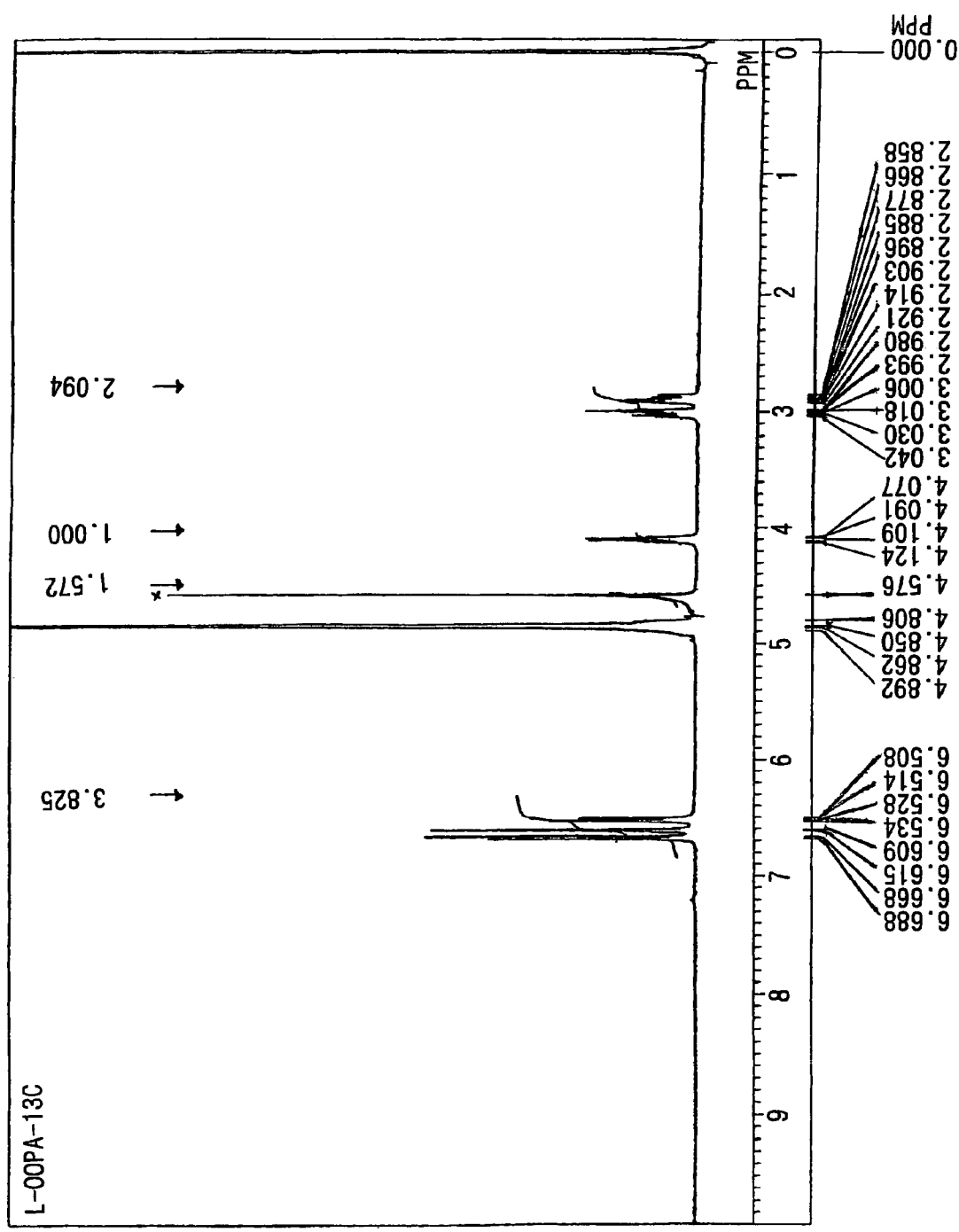
FIG. 1 shows the results of $^1$H-NMR and $^{13}$C-NMR spectrometric analyses for L-[1-$^{13}$C]DOPA.

Hereinbelow, the present invention will be described more specifically with reference to Examples. However, the Examples are illustrative only and the scope of the invention is not limited to those Examples. Rats used in the experiments (male Wistar, 7 weeks old) were purchased from Nippon Charles River.

PRODUCTION EXAMPLE 1

Production of L-[1-$^{13}$C]DOPA

H$_2$O (10 ml) and Ac$_2$O (6.88 g, 64 mmol) were added to [1-$^{13}$C]glycine (MassTrace; 2.44 g, 32 mmol) and stirred at room temperature for 20 minutes. The mixture was allowed to stand in a refrigerator overnight, and the precipitated crystals were filtered out and washed with cold water (3 ml). The filtrate was concentrated under reduced pressure and then added with H$_2$O (2.5 ml), and the resulting mixture was dissolved by heating to reflux. The solution was allowed to stand in a refrigerator overnight, the precipitated crystals were filtered out, washed with cold water (1 ml) and then dried under reduced pressure at 100° C. to yield AcNHCH$_2$$^{13}$CO$_2$H as colorless fine needle-like crystals.

3,4-Dihydroxybenzaldehyde (1.5 g, 10.8 mmol), AcNHCH$_2$$^{13}$CO$_2$H (1.18 g, 10 mmol) and AcONa (2.46 g, 30 mmol) were fully mixed and then added to AcO$_2$ (10 ml). The resulting solution was stirred at 120° C. for 5 hours, and then allowed to stand at room temperature overnight. The reaction solution was added to ice-cold water (500 ml). The precipitated yellow powder was filtered out, washed with water (100 ml) and hot water (20 ml) and then air-dried. Purification by silica gel column chromatography (hexane-EtOH=1:1) yielded [carbonyl-$^{13}$C]2-methyl-4-(3,4-diacetoxybenzal)-5-oxzolone (1.76 g, 58%) as yellow crystals.

[Carbonyl-$^{13}$C]2-methyl-4-(3,4-diacetoxybenzal)-5-oxzolone (1.31 g, 4.3 mmol) and AcNa (1.6 g, 19.5 mmol) were added to MeOH (12 ml) and refluxed for 5 hours. The reaction solution was purified by silica gel column chromatography (CHCl$_3$-MeOH=10:1, AcOEt-MeOH=40:1) to yield a pale yellow amorphous (1.02 g, 64%). The pale yellow amorphous was triturated with an acetone-CHCl$_3$ mixed solution and then re-crystallized to yield [carbonyl-$^{13}$C]methyl α-acetoamide-3,4-dihydroxycinnamate.

To a solution of [carbonyl-$^{13}$C]methyl α-acetoamide-3,4-dihydroxycinnamate (0.618 g, 2.45 mmol) in an EtOH:PhH mixed solution (4:1) (12 ml) in a hydrogen stream was added a solution that had been prepared by dissolving s,s-DIOP (249 mg, 0.5 mmol) and [RhCl(cyclooctene)$_2$]$_2$ (123 mg, 0.25 mmol) in PhH (2 ml) and stirring the solution at room temperature for 15 minutes in a nitrogen stream. The resulting solution was stirred at room temperature for 24 hours, the solvent was distilled away under reduced pressure. Purification by silica gel column chromatography (CHCl$_3$-MeOH=10:1) yielded [carbonyl-$^{13}$C]N-acetyl-3,4-dihydroxyphenylalanine methyl ester as a reddish-brown amorphous (0.5 g, 80%).

[Carbonyl-$^{13}$C]N-acetyl-3,4-dihydroxyphenylalanine methyl ester (0.435 g, 1.71 mmol) was added to 10% HCl (4 ml) and stirred at 120° C. for 3 hours. After the 10% HCl was distilled away under reduced pressure, the residue was added with H$_2$O (5 ml), dried under reduced pressure, further added with H$_2$O (5 ml) and then dried under reduced pressure to yield an amorphous. The amorphous was added with EtOH (6 ml) and dissolved therein, added dropwise with 25% aqueous NH$_3$ under ice-cooling for pH adjustment to 6.5. The solution was allowed to stand in a refrigerator overnight. The precipitated crystals were filtered out, washed with EtOH and Et$_2$O and then dried under reduced pressure to yield pale brown powder (316 mg, 93%). The pale brown powder was added to H$_2$O (7 ml) containing activated carbon and a trace amount of NaHSO$_3$, heated to reflux and then decolorized. The filtrate was allowed to stand in a refrigerator for 3 days to yield colorless prismatic crystals (238 mg, 70%).

Figure 1B:
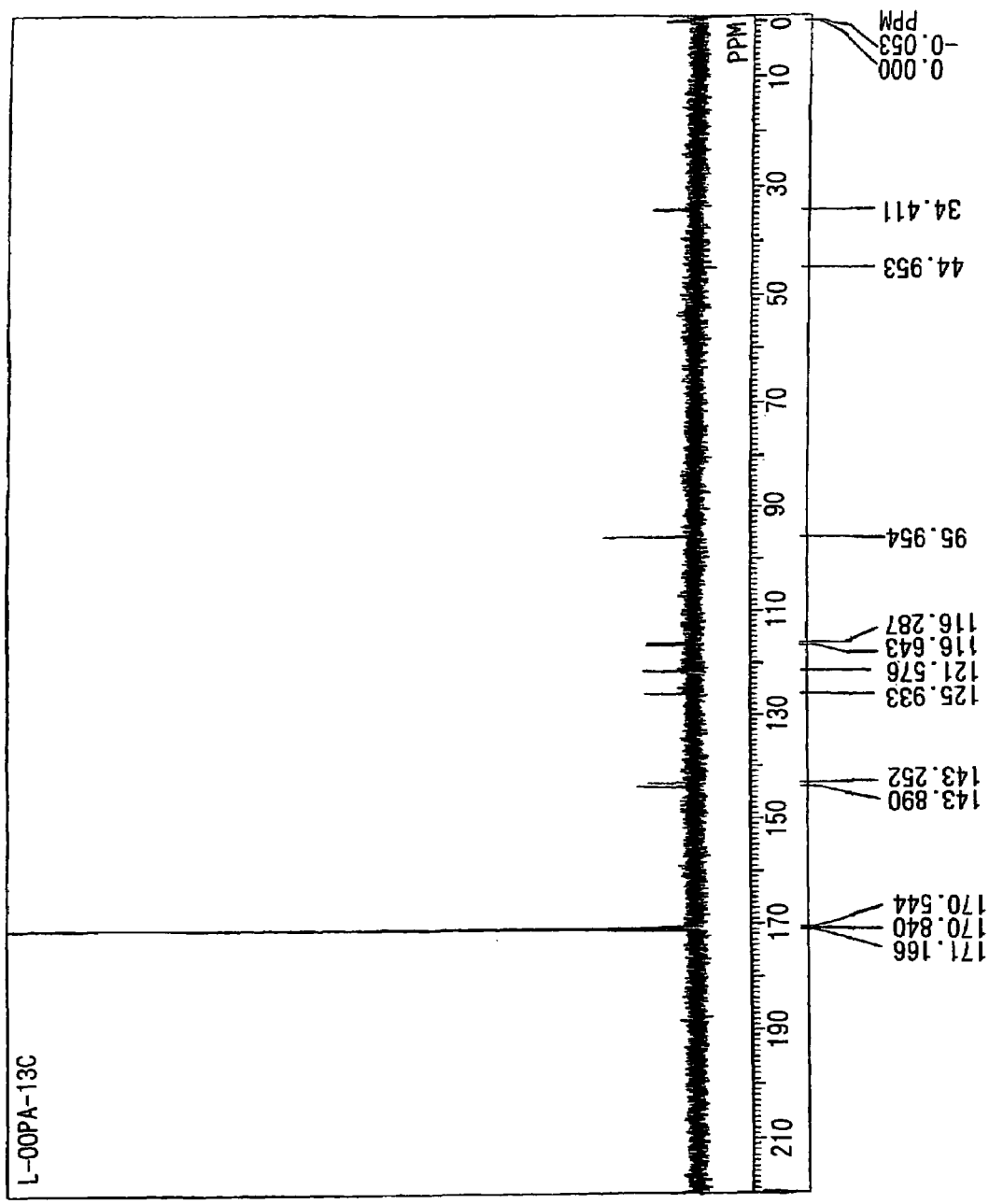

The identification data ($^1$H-NMR and $^{13}$C-NMR spectra) for L-[1-$^{13}$C]DOPA are shown in FIGS. 1(a) and 1(b).

PRODUCTION EXAMPLE 2

Production of Glucosyl [U-$^{13}$C]Glucose (hereinbelow, referred to as "Glc-[U-$^{13}$C]Glc")

Benzyl alcohol (66.7 ml, 645 mmol) and 4.5 N hydrogen chloride-dioxane (9.6 ml, 43.0 mmol) were added to D-glucose-U-$^{13}$C$_6$ (5.00 g, 26.87 mmol, SHOKO) and then heated at 80° C. while stirring. After 50 minutes, the solution was removed from the oil bath, allowed to cool to room temperature, added with ether (1.0 l) and then cooled on ice. The precipitate produced was filtered out, washed with ether and then dried under reduced pressure (yielded amount: 4.52 g, % yield: 60.9%).

Dry acetonitrile (35.0 ml) and dry DMF (7.0 ml) were added to U-$^{13}$C-Glc-OBzl (4.49 g, 16.26 mmol) in an argon atmosphere and dissolved therein. Benzaldehyde dimethyl acetal (3.17 ml, 21.14 mmol) and p-toluensulfonic acid monohydrate (618 mg, 3.25 mmol) were added to the solution and then stirred at room temperature. After 2.5 hours, another portion of benzaldehyde dimethyl acetal (245 μl, 1.63 mmol) was added. After 4.5 hours, saturated aqueous sodium bicarbonate was added to neutralize the solution and then concentrated under reduced pressure to remove acetonitrile. The solution was extracted with ethyl acetate, the organic layers were combined, and then washed with water and saturated saline in turn. The solution was dried over anhydrous magnesium sulfate and filtered, and the filtrate was concentrated under reduced pressure. The residue was dissolved in pyridine (100 ml) and cooled on ice. Anhydrous acetic acid (50 ml, 530 mmol) was added to the solution. After 30 minutes, the solution was removed from the ice bath, and then stirred at room temperature. After 14 hours, the solution was concentrated under reduced pressure, the residue was added with toluene and then distilled azeotropically. This procedure was repeated three times. The residue was purified by silica gel column chromatography to yield 4,6-O-benzylidene-2,3-di-O-acetyl-U-$^{13}$C-Glc-Obzl (yielded amount: 3.31 g, % yield: 45.4%).

4,6-O-Benzylidene-2,3-di-O-acetyl-U-$^{13}$C-Glc-OBzl (1.65 g, 3.68 mmol) was dissolved in dry acetonitrile (33.0 ml), and dimethylamine-borane (1.08 g, 18.4 mmol) was added thereto and dissolved in an argon atmosphere. The reaction mixture was cooled to −40° C., and boron trifluoride etherate (2.33 ml, 18.4 mmol) was added thereto. The reaction mixture was heated gradually to −15° C. over 6 hours and poured into saturated aqueous sodium bicarbonate to neutralize the solution. After the concentration under reduced pressure to remove acetonitrile, the solution was extracted with ethyl acetate, the organic layers were combined and washed with water and saturated saline in turn. The solution was dried over anhydrous magnesium sulfate and filtered, and the filtrate was concentrated under reduced pressure. The residue was purified by silica gel column chromatography to yield 2,3-di-O-acetyl-6-O-benzyl-U-$^{13}$C-Glc-Obzl (yielded amount: 973 mg, % yield: 58.7%).

2,3-Di-O-acetyl-6-O-benzyl-U-$^{13}$C-Glc-OBzl (191 mg, 0.424 mmol) and 2,3,4,6-tetra-O-benzyl-Glc-OC(=NH)—CCl$_3$ (290 mg, 0.424 mmol) were dissolved in dry chloroform (10.0 ml) and then stirred together with Molecular Sieve 4A (500 mg) at room temperature for 15 minutes in an argon atmosphere. The reaction mixture was cooled to −60° C., boron trifluoride etherate (107 μl, 0.848 mmol) was added thereto, and the mixture was heated gradually to −10° C. over 3 hours. The reaction mixture was diluted with ethyl acetate and filtered to remove Molecular Sieve 4A. The resulting solution was washed with ethyl acetate, the filtrate and the washings were combined and then washed with saturated aqueous sodium bicarbonate, water and saturated saline in turn. The solution was dried over anhydrous magnesium sulfate and filtered, and the filtrate was concentrated under reduced pressure. The residue was purified by silica gel column chromatography (yielded amount: 254 mg, % yield: 61.5%). Following this procedure, two more condensation reactions were carried out, yielding 1.01 g of 2',3',4',6'-tetra-O-benzyl-Glc-(α1-4)-2,3-di-O-acetyl-6-O-benzyl-U-$^{13}$C-Glc-OBzl from a total of 967 mg of 2,3-di-O-acetyl-6-O-benzyl-U-$^{13}$C-Glc-OBzl.

2',3',4',6'-Tetra-O-benzyl-Glc-(α1-4)-2,3-di-O-acetyl-6-O-benzyl-U-$^{13}$C-Glc-OBzl (229 mg, 0.235 mmol) was dissolved in dry methanol (10.0 ml), a 5.18 M solution of sodium methoxide in methanol (9.1 μl, 47.0 μmol) was added thereto and stirred at room temperature. After 4 hours, another portion of a 5.18 M solution of sodium methoxide in methanol (4.6 μl, 23.8 μmol) was added and stirred at room temperature for an additional one hour. The reaction solution was added with Amberlyst 15 for neutralization and then filtered. The resin was washed with methanol, the filtrate and the washings were combined and then concentrated under reduced pressure. The residue was purified by silica gel column chromatography (yielded amount: 182 mg, % yield: 87.2%). Deacetylation reaction was carried out again in accordance with this procedure to yield 852 mg of 2',3',4',6'-tetra-O-benzyl-Glc-(α1-4)-6-O-benzyl-U-$^{13}$C-Glc-OBzl from a total of 1.01 g of 2',3',4',6'-tetra-O-benzyl-Glc-(α1-4)-2,3-di-O-acetyl-6-O-benzyl-U-$^{13}$C-Glc-OBzl.

Figure 2:
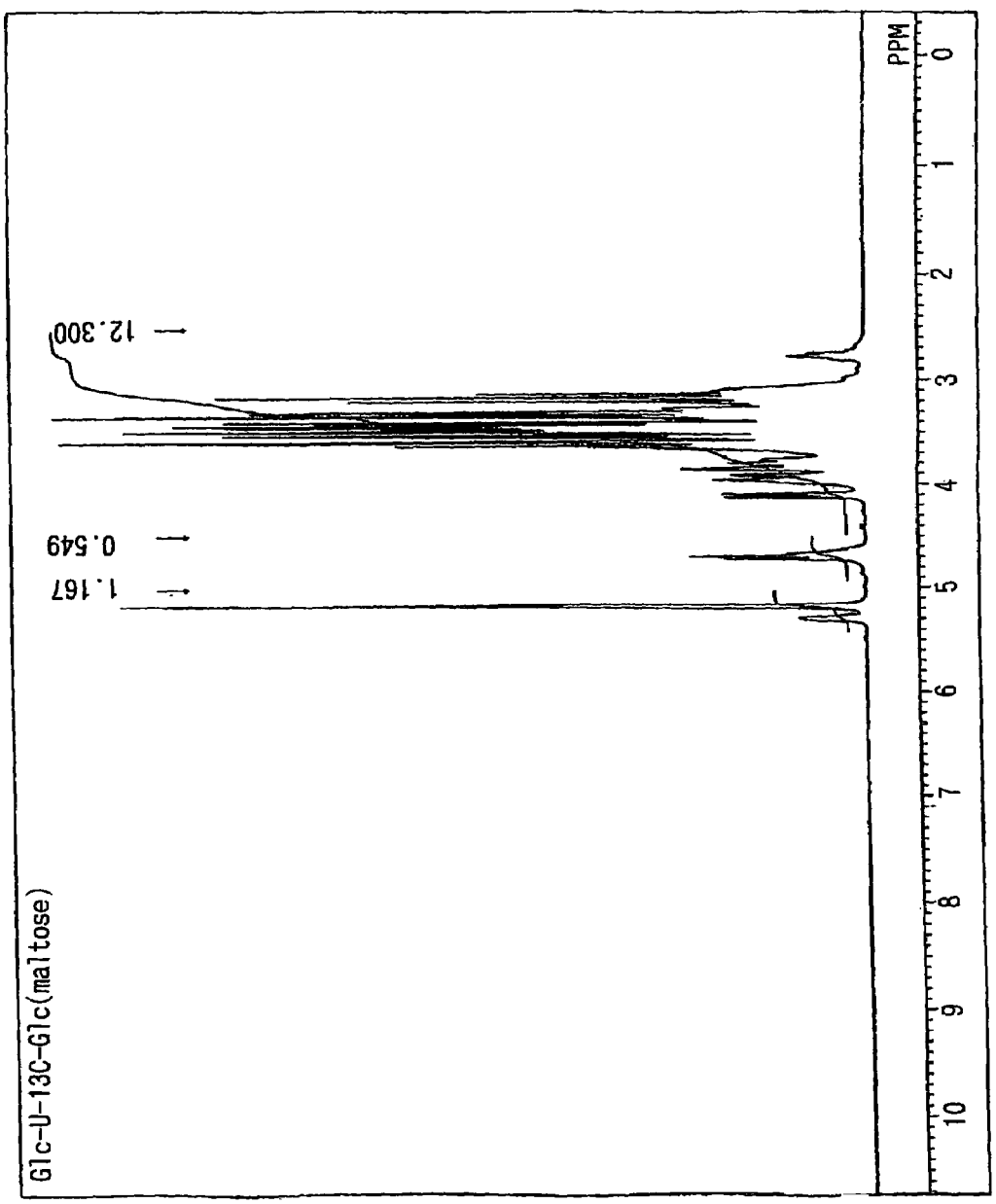
FIG. 2 shows the $^1$H-NMR, $^{13}$C-NMR and ESI-MS spectra for Glc-[U-$^{13}$C]Glc.
Figure 2:
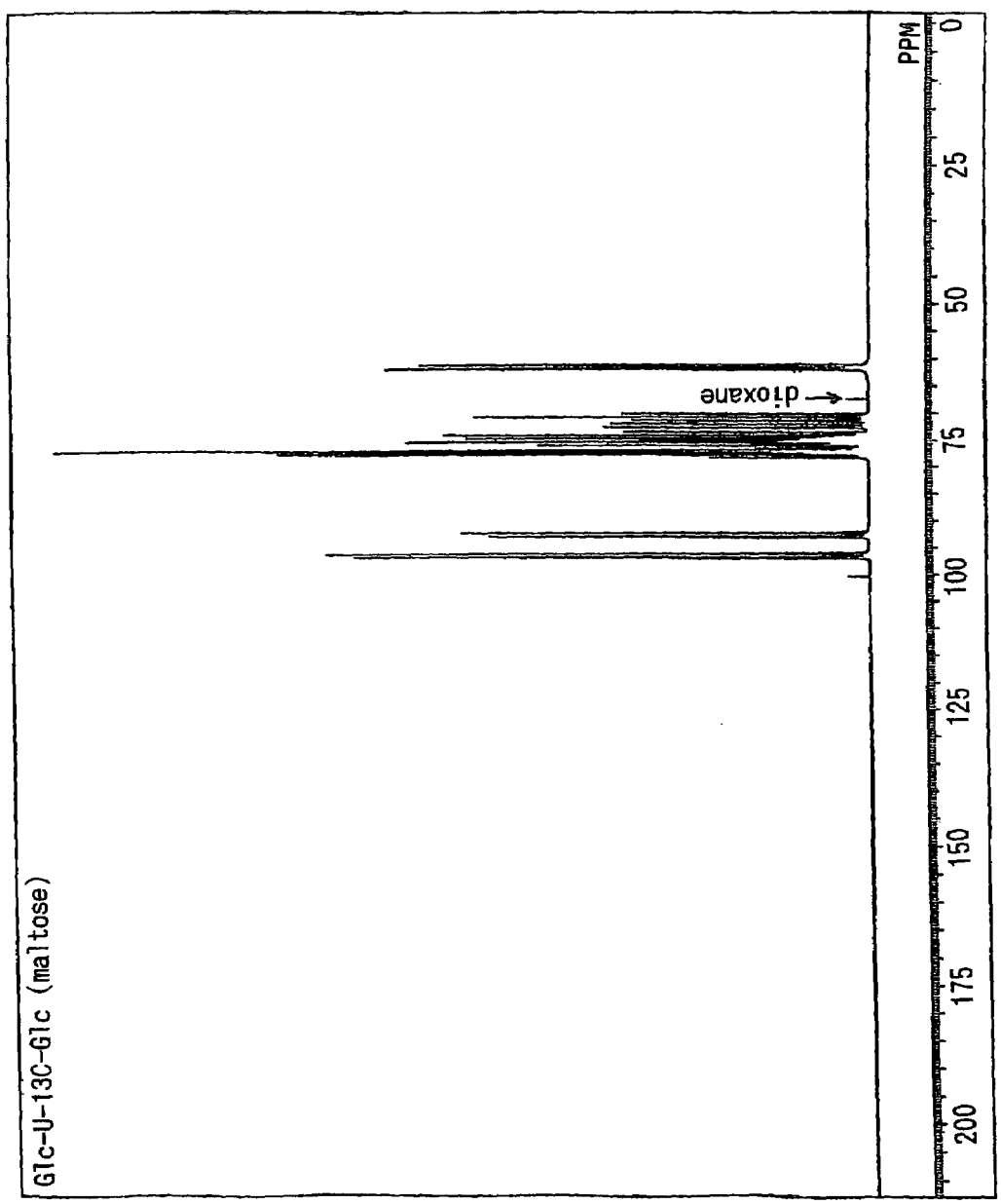
Figure 2:
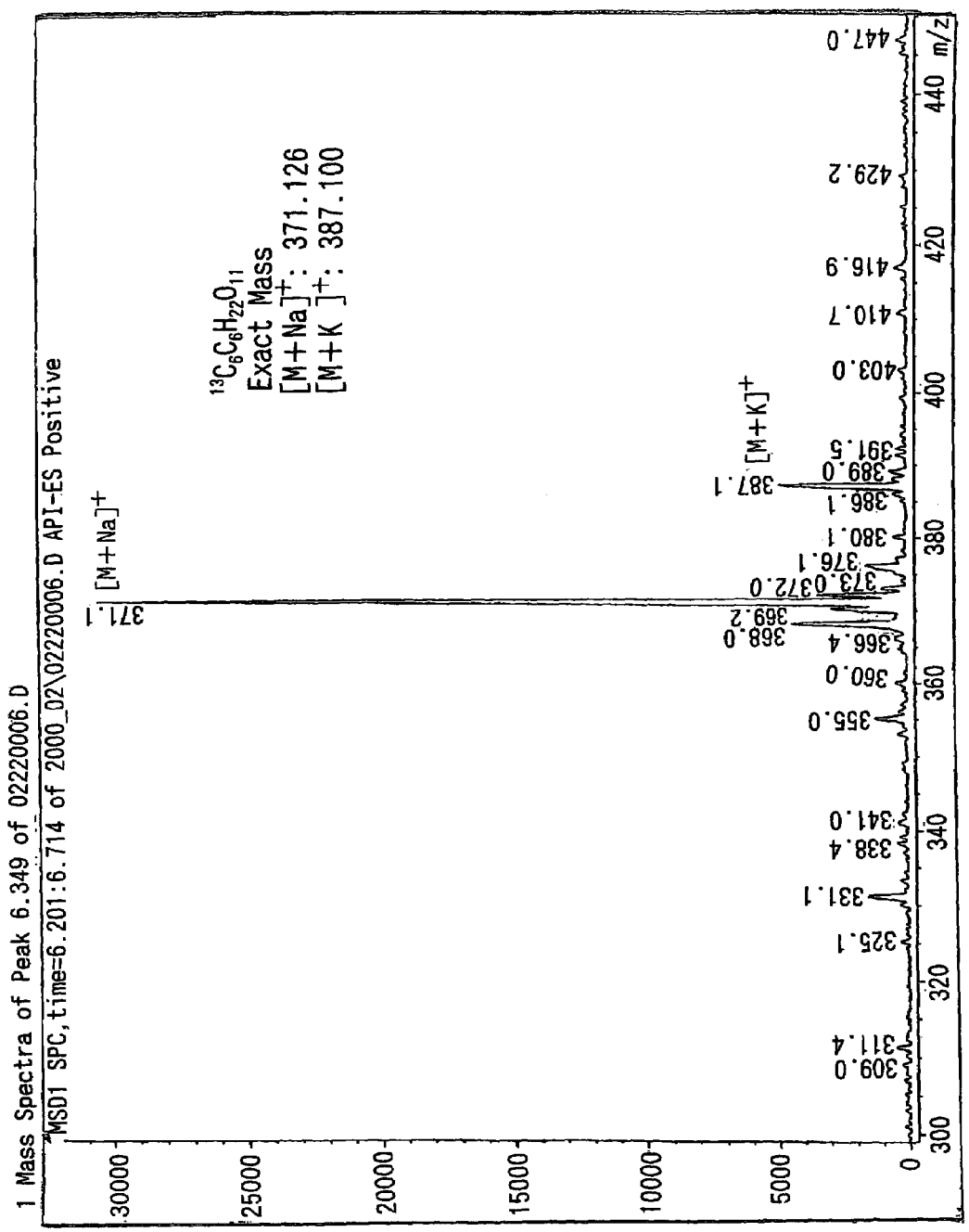

2',3',4',6'-Tetra-O-benzyl-Glc-(α1-4)-6-O-benzyl-U-$^{13}$C-Glc-OBzl (180 mg, 0.202 mmol) was dissolved in methanol (30.0 ml)-water (6.0 ml), palladium black (20 mg) was added thereto, and then purged with hydrogen. After 1 hour, the solution was heated to 35° C. and purged with hydrogen. Water (4.0 ml) was added after 2 hours, and another portion of water (20.0 ml) was added after 4 hours. After 6 hours, the solution was filtered, and the catalyst was washed with water. The filtrate and the washings were combined, concentrated under reduced pressure to remove the methanol and then freeze-dried. The residue was dissolved in water (30 ml), palladium black (20 mg) was added thereto, and the solution was heated to 35° C. and purged with hydrogen. After 6 hours, the solution was filtered, and the catalyst was washed with water. The filtrate and the washings were combined, concentrated under reduced pressure to reduce the liquid volume, and then freeze-dried. The residue was purified by HPLC (TSK-Gel Amide-80) (yielded amount: 61.5 mg, % yield: 87.6%). Reduction reaction was carried out again in accordance with this procedure to yield 290 mg of Glc-[U-$^{13}$C]Glc from a total of 850 mg of 2',3',4',6'-tetra-O-benzyl-Glc-(α1-4)-6-O-benzyl-U-$^{13}$C-Glc-OBzl. The identification data ($^1$H-NMR and $^{13}$C-NMR spectra) for Glc-[U-$^{13}$C]Glc are shown in FIGS. 2(a), 2(b) and 2(c).

PRODUCTION EXAMPLE 3

Production of Benzoyl-Arginyl-[1-$^{13}$C]Alanine (hereinbelow, referred to as "Bz-Arg-[1-$^{13}$C]Ala")

[1-$^{13}$C]Alanine (Masstrace, Inc.) (10.0 g, 0.111 mol) was dissolved in aqueous sodium hydroxide (111 ml), a solution of Boc$_2$O (28.0 ml, 0.122 mol) in acetone (110 ml) and triethylamine (7.71 ml, 55.5 mmol) were added thereto, and then stirred at room temperature overnight. The solution was concentrated under reduced pressure and added with saturated saline to a total volume of 200 ml. The solution was added with citric acid for pH adjustment to 4, saturated with common salt, and then extracted with ethyl acetate four times. The organic layers were washed with saturated saline twice and dried over anhydrous magnesium sulfate. The resulting solution was concentrated under reduced pressure, the residue was dissolved in diethyl ether (150 ml), added with cyclohexylamine (12.7 ml, 0.111 mol), and then allowed to stand at room temperature for 2 hours. The precipitated crystals were filtered out, washed with diethyl ether, and then dried under reduced pressure to yield Boc-[1-$^{13}$C]Ala-OH.CHA.

10% Aqueous citric acid (100 ml) was added to a suspension of Boc-[1-$^{13}$C]Ala-OH.CHA (32.08 g, 0.111 mol) in ethyl acetate (400 ml), stirred at room temperature into a solution and saturated with common salt, and the organic layer was separated from the solution. The resulting solution was extracted with ethyl acetate twice, the organic layers were combined, and then washed with saturated saline twice. The solution was dried over anhydrous magnesium sulfate and concentrated under reduced pressure to yield a colorless extract. The extract was dissolved in ethanol-water (9:1) (200 ml) and added with cesium carbonate (19.0 g, 58.3 mmol). After the foaming ceased, the solution was concentrated under reduced pressure, the residue was added with toluene and then distilled azotropically to remove water, thereby yielding a gel. The gel was suspended in DMF (200 ml), added with benzyl bromide (13.2 ml, 0.111 mol), and stirred at room temperature for 12 hours. The solution was concentrated under reduced pressure, the residue was added with ethyl acetate, washed with water, 10% aqueous citric acid, saturated saline, saturated aqueous sodium bicarbonate and saturated saline in turn, and dried over anhydrous magnesium sulfate. Ethyl acetate was distilled away from the solution under reduced pressure to yield Boc-[1-$^{13}$C]Ala-OBzl.

4.5 N Hydrogen chloride/dioxane (250 ml) was added to Boc-[1-$^{13}$C]Ala-OBzl (31.27 g, 0.111 mol) and then allowed to stand at room temperature for 30 minutes. After the concentration under reduced pressure, diethyl ether (200 ml) was added, and the precipitated crystals were filtered out and dried under reduced pressure to yield HCl.H-[1-$^{13}$C]Ala-OBzl (22.48 g).

HCl.H-[1-$^{13}$C]Ala-OBzl (700 mg, 3.23 mmol), Boc-Arg(Tos).⅘AcOEt.¼H$_2$O (1.63 g, 3.23 mmol) and HOBt (459 mg, 3.39 mmol) were dissolved in DMF (8 ml), added dropwise with WSCD (602 μl, 3.39 mmol) while stirring under ice-cooling, and stirred under ice-cooling for 30 minutes and then at room temperature for 3 hours. The solution was added with ethyl acetate, washed with saturated aqueous sodium bicarbonate, water, 10% aqueous citric acid and water in turn and dried over magnesium sulfate. Ethyl acetate was distilled away from the solution under reduced pressure, the residue was added with diisopropyl ether-hexane, the precipitated solid was filtered and dried under reduced pressure to yield Boc-Arg(Tos)-[1-$^{13}$C]Ala-OBzl (1.78 g, 91%).

6 N Hydrogen chloride/dioxane (30 ml) was added to Boc-Arg(Tos)-[1-$^{13}$C]Ala-OBzl (1.78 g, 2.94 mmol) and stirred at room temperature for 1 hour. Ethyl acetate was added to the solution, and the solution was washed with saturated aqueous sodium bicarbonate, water, 10% aqueous citric acid and water in turn and dried over anhydrous magnesium sulfate. Ethyl acetate was distilled away from the solution under reduced pressure, the residue was added with diethyl ether-hexane, and the precipitated solid was filtered out and dried under reduced pressure to yield Bz-Arg(Tos)-[1-$^{13}$C]Ala-OBzl (1.63 g, 91%).

Anhydrous hydrogen fluoride (8.5 ml) was charged into a mixture of Bz-Arg(Tos)-[1-$^{13}$C]Ala-OBzl (1.63 g, 2.74 mmol) and anisole (1.5 ml, 13.9 mmol) while stirring under cooling in a dry ice-methanol bath, and then stirred for 1 hour under ice-cooling. Hydrogen fluoride was distilled away from the solution under ice-cooling, the solution was added with water (20 ml) and diethyl ether (10 ml) and stirred, and the aqueous layer was removed and concentrated under reduced pressure. The residue was dissolved in water (30 ml), a trace amount of the insoluble substance was filtered off, and the filtrate was purified by RP-HPLC (YMC-PAK ODS 10 μm, 30×250 mm, 1-60% MeCN (containing 0.1% TFA), 80 min., 20 ml/min). After the main fractions were collected and freeze-dried, the residue was dissolved in water (30 ml), exchanged into acetate with a strong ionic anion exchange resin (Muromac 1×2, AcO⁻ form, 20 ml), and then freeze-dried to yield Bz-Arg-[1-$^{13}$C]Ala as colorless powder (774 mg, 81%).

Figure 3:
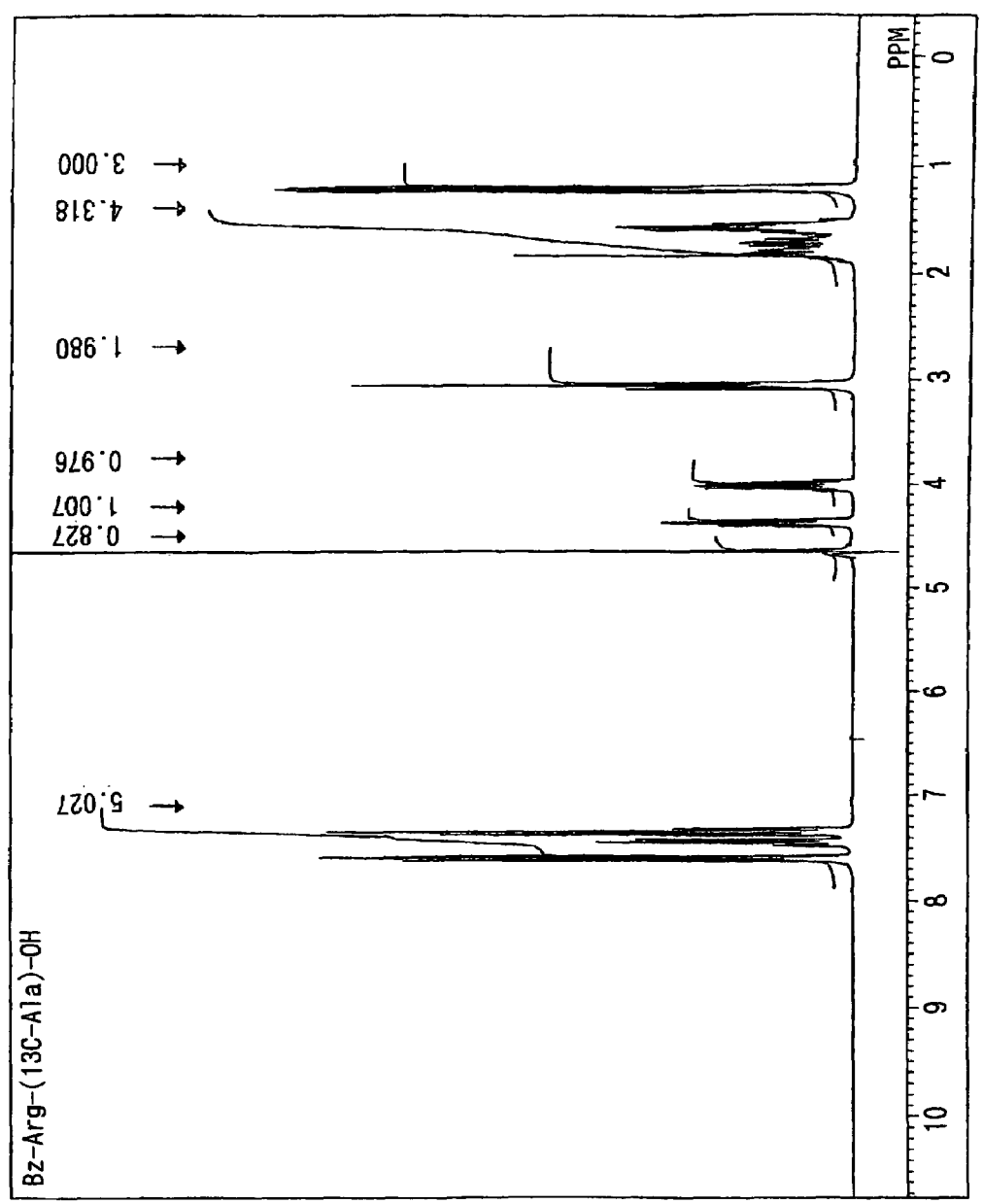
FIG. 3 shows the results of $^1$H-NMR and $^{13}$C-NMR spectrometric and HPLC analyses for Bz-Arg-[1-$^{13}$C]Ala.
Figure 3:
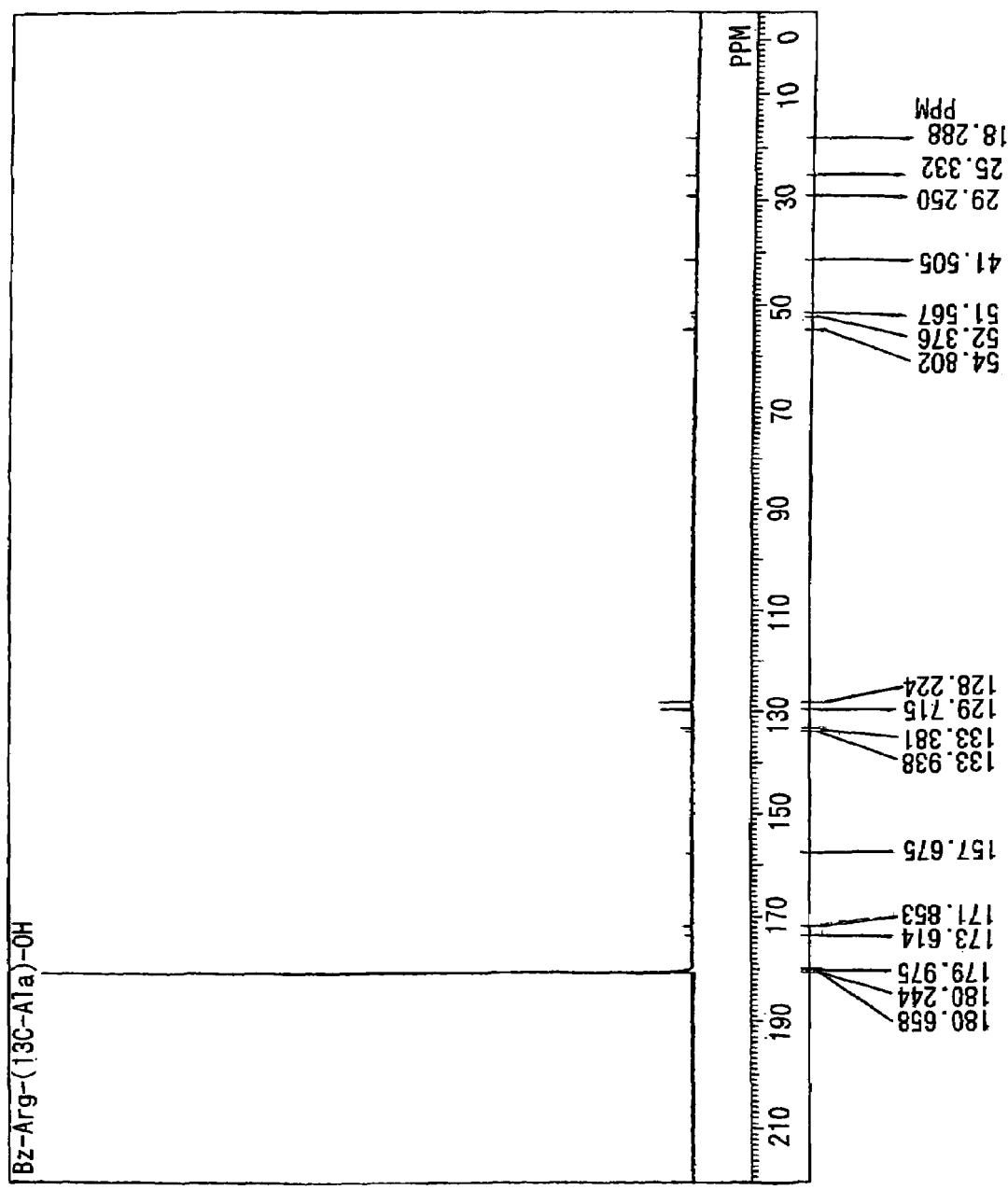
Figure 3:
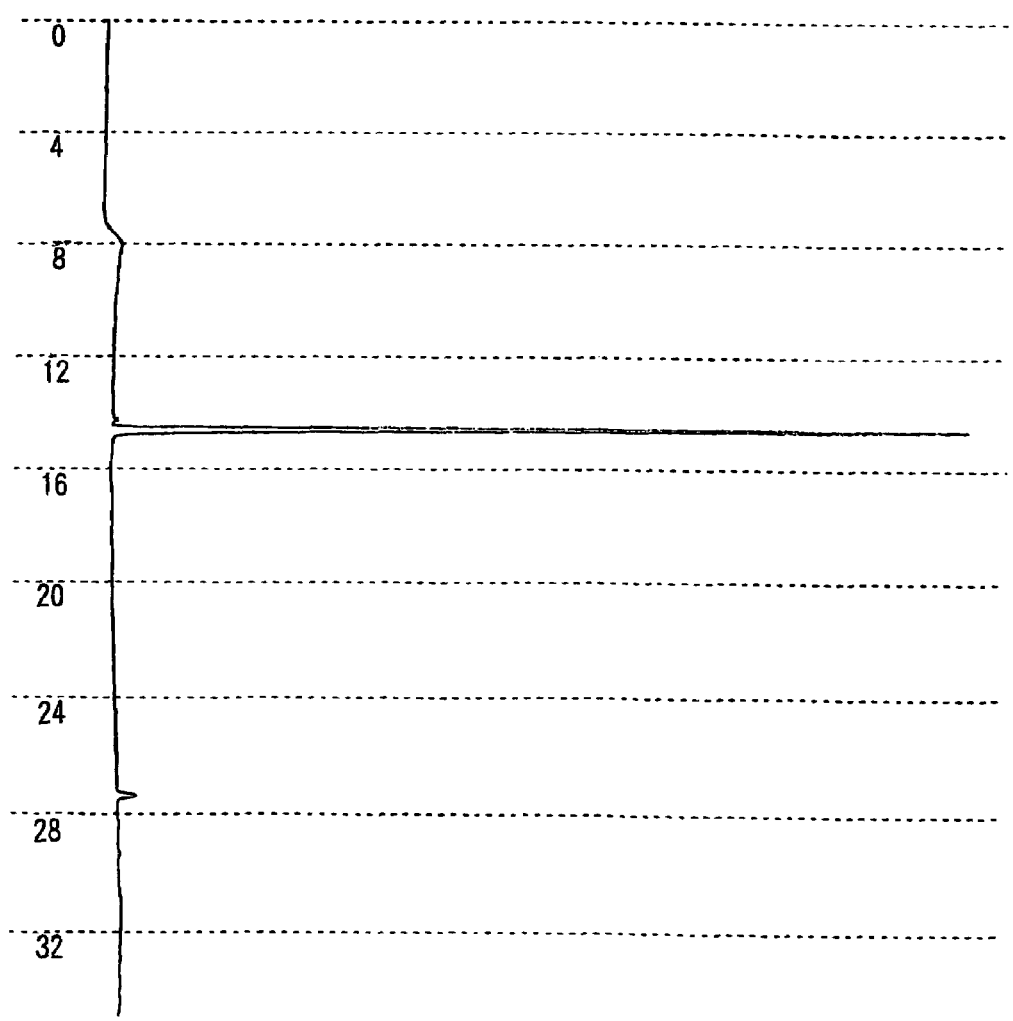

The identification data ($^1$H-NMR and $^{13}$C-NMR spectra, HPLC analysis chart) for Bz-Arg-[1-$^{13}$C]Ala are shown in FIGS. 3(*a*), 3(*b*) and 3(*c*).

PRODUCTION EXAMPLE 4

Production of [U-$^{13}$C]γ-Cyclodextrin

Figure 4:
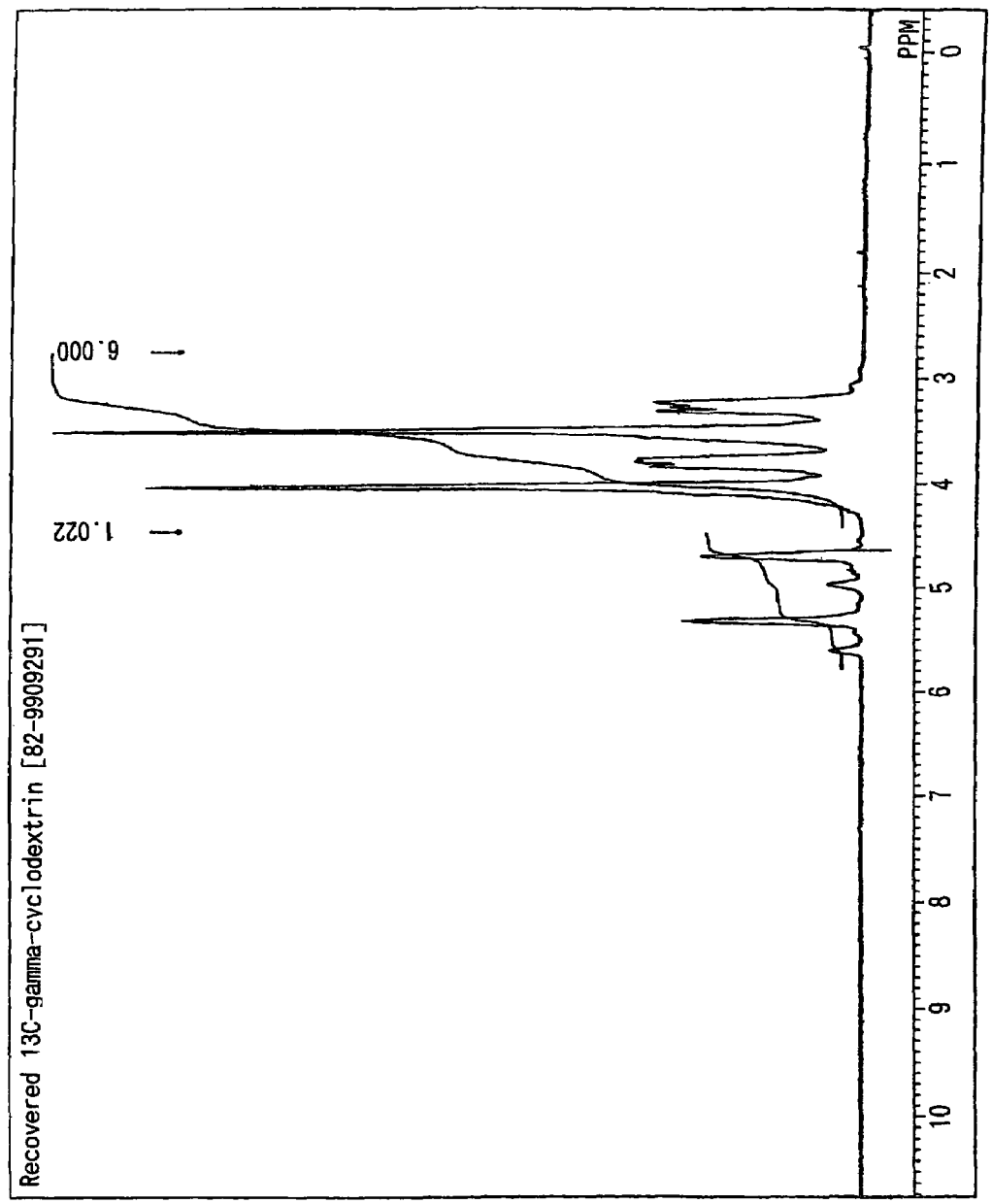
FIG. 4 shows the $^1$H-NMR, $^{13}$C-NMR and ESI-MS spectra for [U-$^{13}$C]γ-Cyclodextrin.
Figure 4:
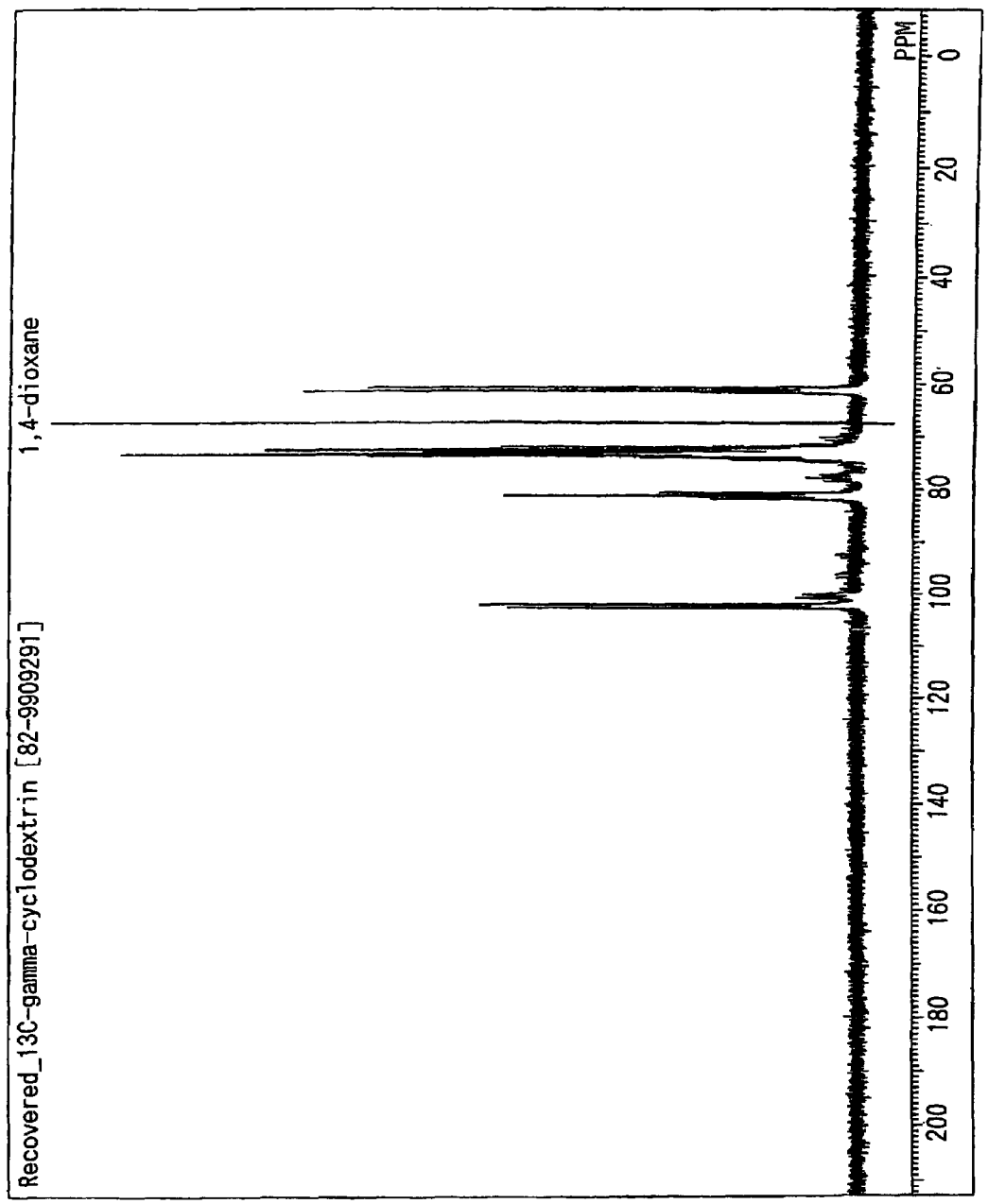
Figure 4:
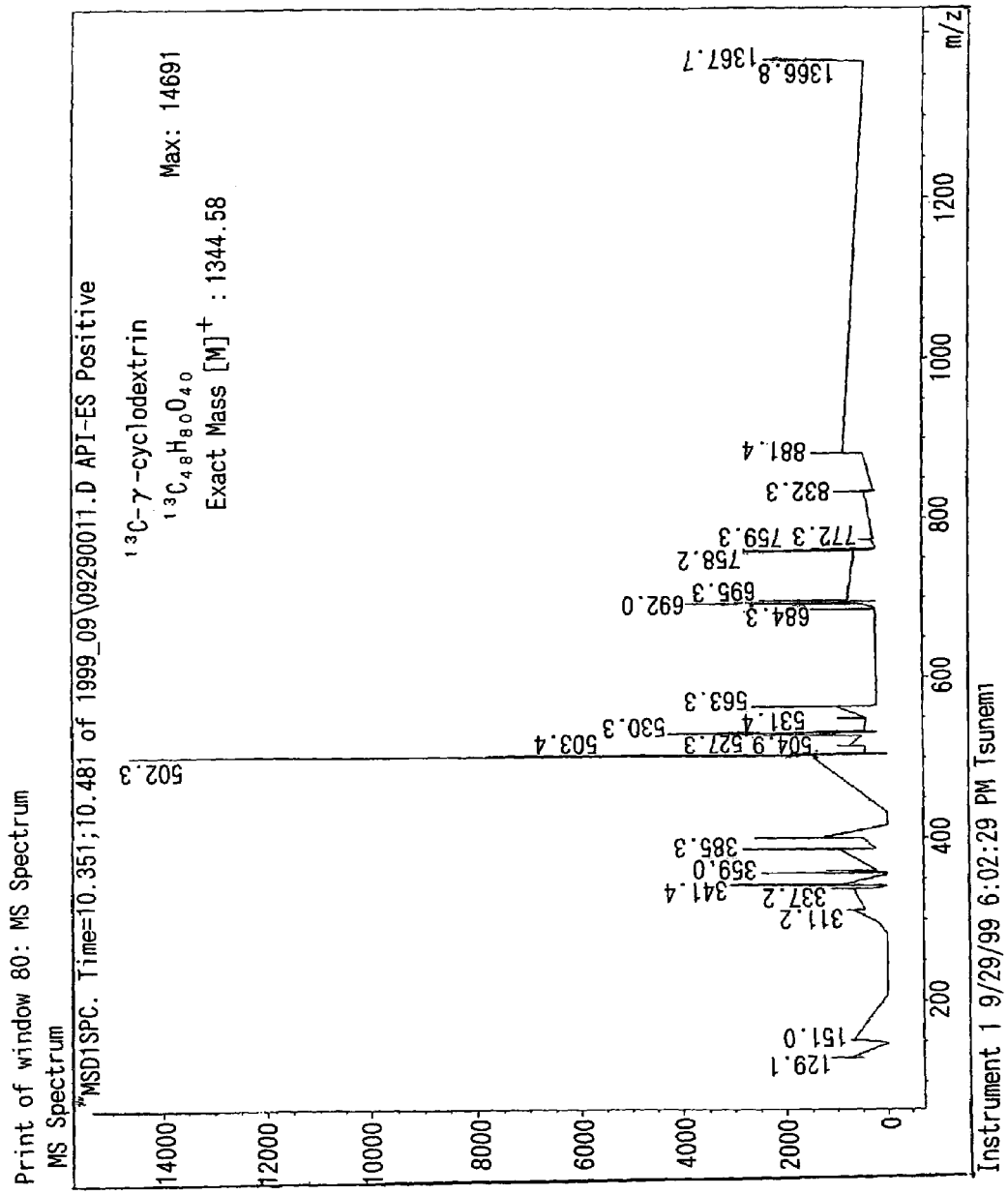

[U-$^{13}$C]starch (Chlorella Kogyo Co., Ltd.; Algal Starch (water-soluble), Lot No. 8031,S, U-13C:98.6 atom %, Starch Content: 93.5%, 4.65 g) was dissolved in 50 mM acetate buffer (pH 5.4) at a concentration of 0.5% (w/v), cyclomaltodextrin glucanotransferase (Hayashibara Biochemical Laboratories Inc.) (186 units) was added thereto. The solution was allowed to react at 40° C. for 2 hours and 20 minutes and then treated at 95° C. for 15 minutes to deactivate the enzyme. This procedure was repeated four times, and the resulting reaction solution was applied on Sephadex G-25 to separate the fractions containing [U-$^{13}$C]γ-cyclodextrin. The freeze-dried substance (1.4 g) was purified in 6 portions by HPLC (TSK-Gel Amide-80 column). The [U-$^{13}$C]γ-cyclodextrin fractions were freeze-dried to give the product (398 mg). The identification data ($^1$H-NMR, $^{13}$C-NMR and ESI-MS spectra) for [U-$^{13}$C]γ-cyclodextrin are shown in FIGS. 4(*a*), 4(*b*) and 4(*c*).

EXAMPLE 1

Pharmacological Effect Diagnostic Reagent for a Component of Anti-Parkinson Agent Benserazide ([1-$^{13}$C]DOPA) and Screening Reagent for Evaluating the Degree of Inhibition or Enhancement of DOPA Decarboxylase: [1-$^{13}$C]DOPA (Substance to be Evaluated: A Component of Anti-Parkinson Agent Benserazide The pharmacological effect of benserazide is the inhibition of DOPA decarboxylase. [1-$^{13}$C]DOPA (see Production Example 1) which is a substrate for DOPA decarboxylase is provided as a pharmacological effect diagnostic reagent and a screening reagent. Comparison was made in the [1-$^{13}$C] DOPA breath test on rats which were administered intraperitoneally with benserazide hydrochloride (Sigma) at a dose of 50 mg/kg three times (i.e., in the morning and evening of the day before the [1-$^{13}$C]DOPA breath test and 30 minutes before the breath test was started on the day of the test) (administration group) and rats without administration (control group). The [1-$^{13}$C]DOPA breath test was carried out under anesthesia and [1-$^{13}$C]DOPA was administered at a dose of 50 mg/kg through the femoral vein, and the time course of the degree of increase of the $^{13}$C level in exhaled $CO_2$ ($\Delta^{13}$C (‰)) was measured.

The rats of the administration group and the control group which had been fasted overnight were fixed supinely under anesthesia. The breath was collected at a rate of about 100 to 300 ml/min using a stroke pump (Variable Stroke Pump VS-500, Shibata Kagaku Kogyo) and introduced directly to the flow cell of a $^{13}CO_2$ analyzer EX-130S (Nihon Bunko). A Perma Pure drier (MD-050-12P, Perma Pure INC.) was placed between the rat holder and the stroke pump to remove water vapor from the breath. When the $CO_2$ concentration stabilized, [1-$^{13}$C]DOPA was administered at a dose of 50 mg/kg through the femoral vein. The $CO_2$ concentration in the collected breath was held at 3±0.5%.

Output data from the $^{13}CO_2$ analyzer were AD-converted and input to a personal computer (Apple Power Macintosh 8500). Using data processing software Lab VIEW (National Instruments), 10 pieces of data were integrated and averaged every 100 msec at intervals of 5 seconds and converted to $^{13}$C atom %, $\Delta^{13}$C (‰) and $CO_2$ concentration (%). In this manner, the $^{13}$C-breath test was continuously carried out. The converted data were displayed real-time and stored in a hard disc.

$\Delta^{13}$C (‰) was calculated from the $^{13}$C level in the exhaled $CO_2$ at each time point ($^{13}C_{tmin}$) and the $^{13}$C level in the standard $CO_2$ ($^{13}C_{std}$) according to the following equation:

$$\Delta^{13}C(‰)=[(^{13}C_{tmin}-^{13}C_{0min})/^{13}C_{std}]\times 1000$$

Figure 5:
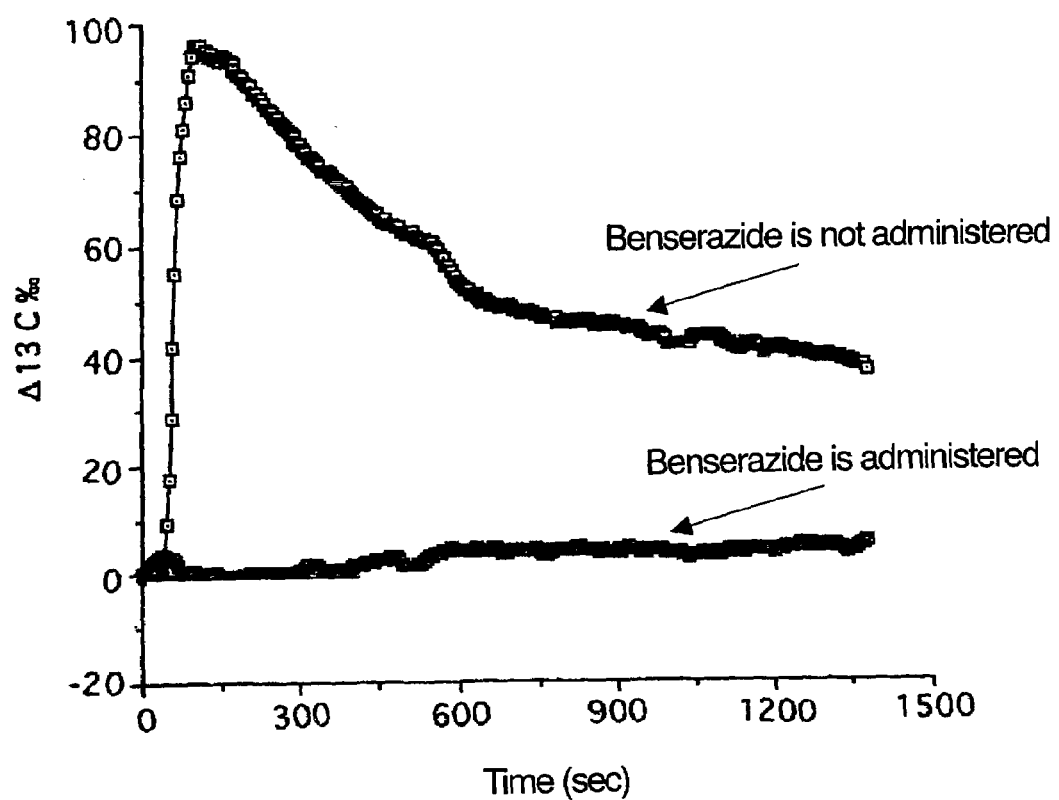
FIG. 5 shows the time course of the [1-$^{13}$C]DOPA breath test.

The results of the [1-$^{13}$C]DOPA breath test were as follows: in the control group, the $\Delta^{13}$C increased rapidly after the administration, reached 100‰ in peak value two minutes after the administration and then gradually decreased with the elapse of time; in the administration group, the $\Delta^{13}$C (‰) showed little increase after the administration and was as low as about 5‰ even 20 minutes after the administration (FIG. 5). From the results, it was confirmed that the function of the target enzyme for benserazide was almost 100% inhibited under the benserazide administration conditions of the present example. Accordingly, by using [1-$^{13}$C]DOPA as a pharmacological effect diagnostic reagent, it becomes possible to evaluate the pharmacological effect of benserazide. In addition, by using [1-$^{13}$C]DOPA as a screening reagent, it becomes possible to provide the method and the reagent for screening for a DOPA decarboxylase-targeting pharmaceutical agent having stronger effect and/or a prodrug thereof.

EXAMPLE 2

Pharmacological Effect Diagnostic Reagent for Anti-Diabetes Agent Acarbose (Glc-[U-$^{13}$C]Glc) and Screening Reagent for Evaluating the Degree of Inhibition or Enhancement of α-Glucosidase: Glc-[U-$^{13}$C]Glc (Substance to be Evaluated: Anti-Diabetes Agent Acarbose)

The pharmacological effect of acarbose is the inhibition of α-glucosidase. Glc-[U-$^{13}$C]Glc (see Production Example 2) which is a substrate for α-glucosidase is provided as a pharmacological effect diagnostic reagent and a screening reagent. The time course of the degree of increase of the $^{13}$C level in exhaled $CO_2$ ($\Delta^{13}$C (‰)) after the administration of Glc-[U-$^{13}$C]Glc was measured and compared on rats which were administered orally with acarbose (trade name: Glucobay, Bayer Corporation) (2 mg/kg, 4 mg/kg or 10 mg/kg) concurrently with the oral administration of Glc-[U-$^{13}$C]Glc (25 mg/kg) and rats which were administered with Glc-[U-$^{13}$C]Glc alone (acarbose 0 mg/kg group).

The rats (male Wistar, 8 weeks old) fasted overnight were fixed in a rat holder for microwave irradiation system without anesthesia. The breath was collected at a rate of about 100 to 300 ml/min using a stroke pump (Variable Stroke Pump VS-500, Shibata Kagaku Kogyo), and the $CO_2$ concentration in the collected breath was held at about 3%. A Perma Pure drier (MD-050-12P, Perma Pure INC.) was placed between the rat holder and the stroke pump to remove water vapor from the breath. When the $CO_2$ concentration stabilized, the rats were taken out from the rat holder and Glc-[U-$^{13}$C]Glc dissolved in distilled water was administered to the rats through the stomach using a tube adapted to oral administration (dose amount: 35 µmol/kg (5 ml/kg)). The breath was sampled with a syringe until the time point of 20 minutes at intervals of 5 minutes. Fifteen ml of the breath was sampled through the syringe into a vacuum vial (10 ml) and sealed, and then subjected to automated analysis by GC-MS (Breath MAT) [FinniganMAT]. The $\Delta^{13}C$ (‰) was calculated from the $\delta^{13}C$ which is the $^{13}C$ value for the breath sample (a difference from the $^{13}C$ value for the standard substance PDB) according to the following equation:

$$\Delta^{13}C(‰)=(\delta^{13}C)_{tmin}-(\delta^{13}C)_{0min}$$

<Measurement conditions for Breath MAT>
  Apparatus: Breath MAT plus (Finnigan)
  Carrier gas: He
  Measurement ion: m/z=44, 45, 46

Figure 6:
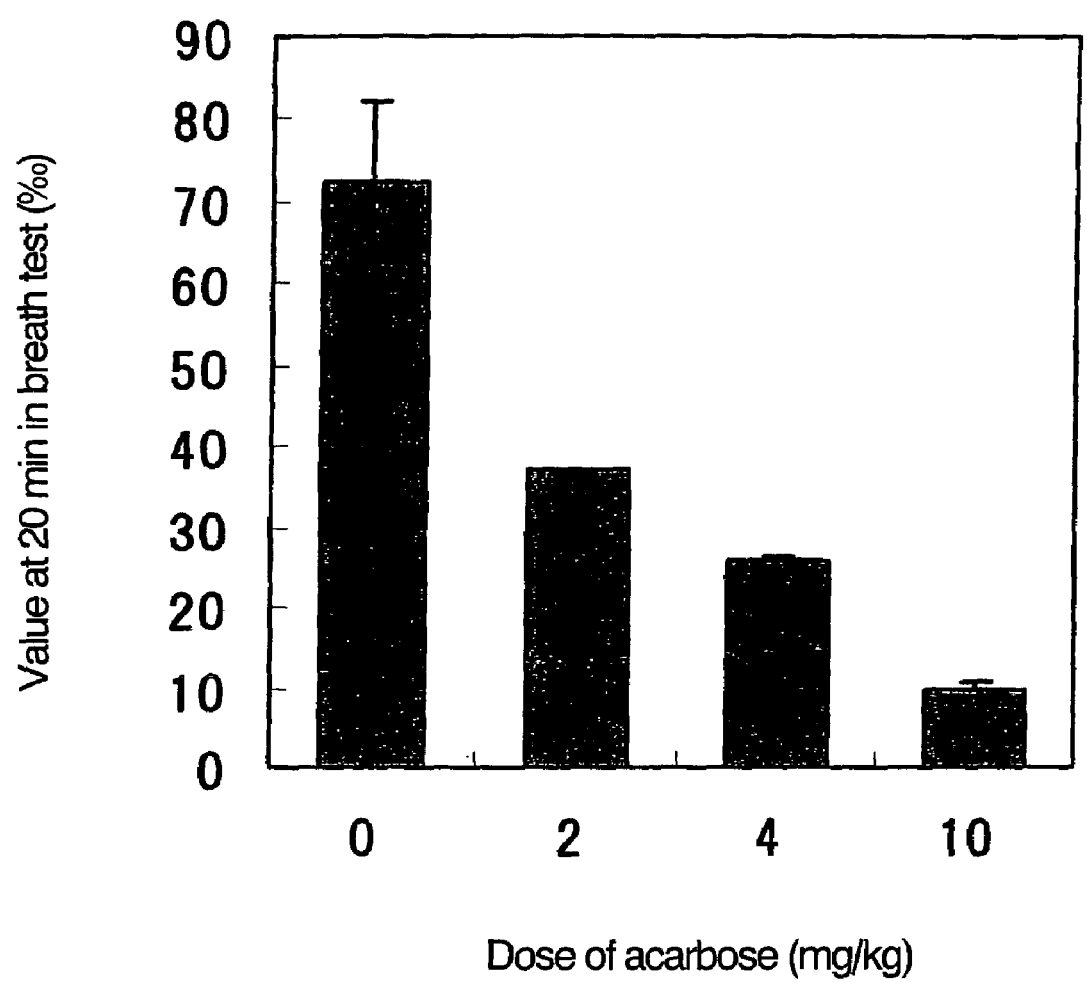
FIG. 6 shows the comparison of the values at the time point of 20 minutes in the glucosyl [U-$^{13}$C]glucose breath test.

The results of the Glc-[U-$^{13}$C]Glc breath test were as follows: in all groups, the $\Delta^{13}C$ increased linearly; in the 0 mg/kg group (n=2), the $\Delta^{13}C$ reached 72.60 ±9.47‰ in 20 minutes, in contrast, the $\Delta^{13}C$ reached 37.06 ±0.16‰ in the 2 mg/kg group (n=2), reached 26.01 ±0.38‰ in the 4 mg/kg group (n=2) and reached 9.86±0.66‰ in the 10 mg/kg group (n=2); thus, the $\Delta^{13}C$ decreased with increasing dose amount (FIG. 6). From the results, it was confirmed that the function of the target enzyme for acarbose was inhibited in a dose dependent manner under the acarbose administration conditions of the present example. Accordingly, by using Glc-[U-$^{13}$C]Glc as a pharmacological effect diagnostic reagent, it becomes possible to evaluate the pharmacological effect of acarbose. In addition, by using Glc-[U-$^{13}$C]Glc as a screening reagent, it becomes possible to provide the method and the reagent for screening for an α-glucosidase-targeting pharmaceutical agent having stronger effect and/or a prodrug thereof.

EXAMPLE 3

Pharmacological Effect Diagnostic Reagent for Anti-Pancreatitis Agent Camostat Mesylate (Bz-Arg-[1-$^{13}$C]Ala) and Screening Reagent for Evaluating the Degree of Inhibition or Enhancement of Pancreatic Protease: Bz-Arg-[1-$^{13}$C]Ala (Substance to be Evaluated: Anti-Pancreatitis Agent Camostat Mesylate)

Figure 7:
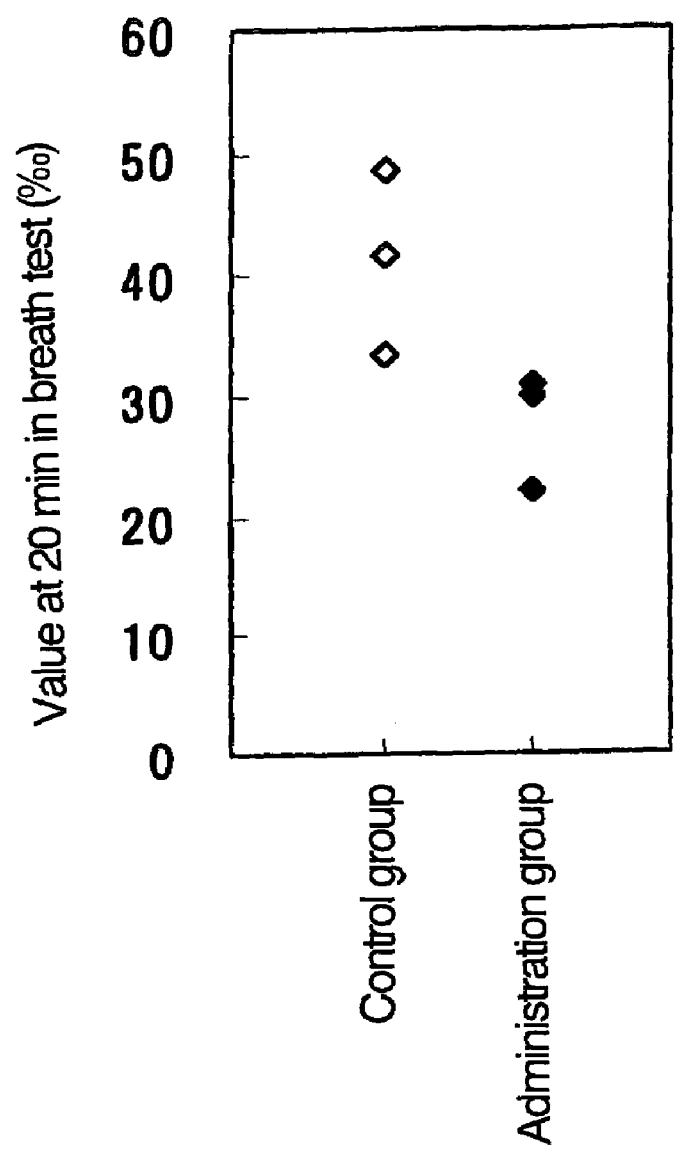
FIG. 7 shows the comparison of the values at the time point of 20 minutes in the Bz-Arg-[1-$^{13}$C]Ala breath test.

The pharmacological effect of camostat mesylate is the inhibition of pancreatic protease. Bz-Arg-[1-$^{13}$C]Ala (see Production Example 3) which is a substrate for pancreatic protease is provided as a pharmacological effect diagnostic reagent and a screening reagent. The time course of the degree of increase of the $^{13}C$ level in exhaled $CO_2$ ($\Delta^{13}C$ (‰)) after the administration of Bz-Arg-[1-$^{13}$C]Ala was measured and compared in the same manner as in Example 2 on rats which were administered orally with camostat mesylate (trade name: Foipan, Ono Pharmaceutical Co., Ltd.) (20 mg/kg) concurrently with the oral administration of Bz-Arg-[1-$^{13}$C]Ala (12.2 mg/kg) (administration group) and rats which were administered with Bz-Arg-[1-$^{13}$C]Ala alone (control group). The results of the Bz-Arg-[1-$^{13}$C]Ala breath test were as follows: in the both groups, the $\Delta^{13}C$ increased linearly until at the time point of 15 minutes after the administration; twenty minutes after the administration, the $\Delta^{13}C$ reached 41.29±7.49‰ in the control group (n=3), while the $\Delta^{13}C$ reached 27.64±4.86‰ in the administration group (n=3); thus, the $\Delta^{13}C$ decreased in the administration group (FIG. 7). From the results, it was confirmed that the function of the target enzyme for camostat mesylate was inhibited under the camostat mesylate administration conditions of the present example. Accordingly, by using Bz-Arg-[1-$^{13}$C]Ala as a pharmacological effect diagnostic reagent, it becomes possible to evaluate the pharmacological effect of camostat mesylate. In addition, by using Bz-Arg-[1-$^{13}$C]Ala as a screening reagent, it becomes possible to provide the method and the reagent for screening for a pancreatic-protease-targeting pharmaceutical agent having stronger effect and/or a prodrug thereof.

EXAMPLE 4

Pharmacological Effect Diagnostic Reagent for Digestive Agent Taka-Diastase ([U-$^{13}$C]γ-Cyclodextrin) and Screening Reagent for Evaluating the Degree of Inhibition or Enhancement of Amylase: [U-$^{13}$C]γ-cyclodextrin (Substance to be evaluated: digestive agent Taka-Diastase)

Figure 8:
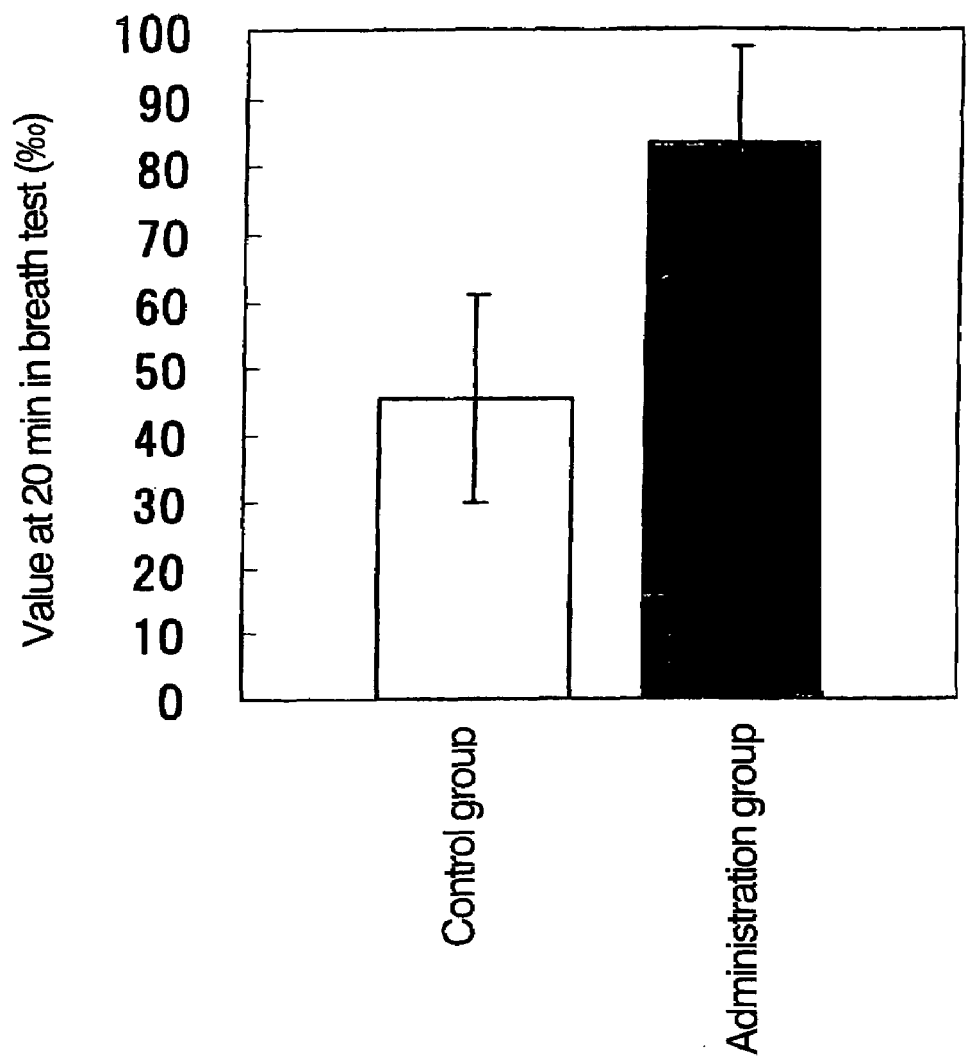
FIG. 8 shows the comparison of the values at the time point of 20 minutes in the [U-$^{13}$C]γ-cyclodextrin breath test.

Taka-Diastase is one of amylases and corresponds to a medicine comprising an enzyme. It has been used as a digestive agent for supporting the function of an amylase in a living body (target enzyme). Accordingly, the pharmacological effect of Taka-Diastase is the enhancement of amylase. [U-$^{13}$C]γ-cyclodextrin (see Production Example 4) which is a substrate for Taka-Diastase and the amylase in a living body is provided as a pharmacological effect diagnostic reagent and a screening reagent. The time course of the degree of increase of the $^{13}C$ level in exhaled $CO_2$ ($\Delta^{13}C$ (‰)) after the administration of [U-$^{13}$C]γ-cyclodextrin was measured and compared in the same manner as in Example 2 on rats which were administered orally with [U-$^{13}$C]γ-cyclodextrin (40 mg/kg) 5 minutes after the oral administration of Taka-Diastase (trade name: Takadiastase, Sankyo Co., Ltd.) (6 mg/kg) (administration group) and rats which were administered with [U-$^{13}$C]γ-cyclodextrin alone (control group). The results of the [U-$^{13}$C]γ-cyclodextrin breath test were as follows: in the both groups, the $\Delta^{13}C$ increased linearly until at the time point of 30 minutes after the administration; twenty minutes after the administration, the $\Delta^{13}C$ reached 45.46±15.57‰ in the control group (n=2), while the $\Delta^{13}C$ reached 83.66±13.87‰ in the administration group (n=2); thus, the $\Delta^{13}C$ increased in the administration group (FIG. 8). From the results, it was confirmed that Taka-Diastase enhanced the function of the target enzyme amylase under the Taka-Diastase administration conditions of the present example. Accordingly, by using [U-$^{13}$C]γ-cyclodextrin as a pharmacological effect diagnostic reagent, it becomes possible to evaluate the pharmacological effect of Taka-Diastase. In addition, by using [U-$^{13}$C]γ-cyclodextrin as a screening reagent, it becomes possible to provide the method and the reagent for screening for an amylase-targeting pharmaceutical agent having stronger effect and/or a prodrug thereof.

EXAMPLE 5

Pharmacological Effect Diagnostic Reagent for H1-Receptor-Antagonist Agent ([1,2-$^{13}$C]Ornithine) and Screening Reagent for Evaluating the Degree of Inhibition or Enhancement of H1 Receptor: [1,2-$^{13}$C]Ornithine (Substance to be Evaluated: Chlorpheniramine Maleate)

Figure 9:
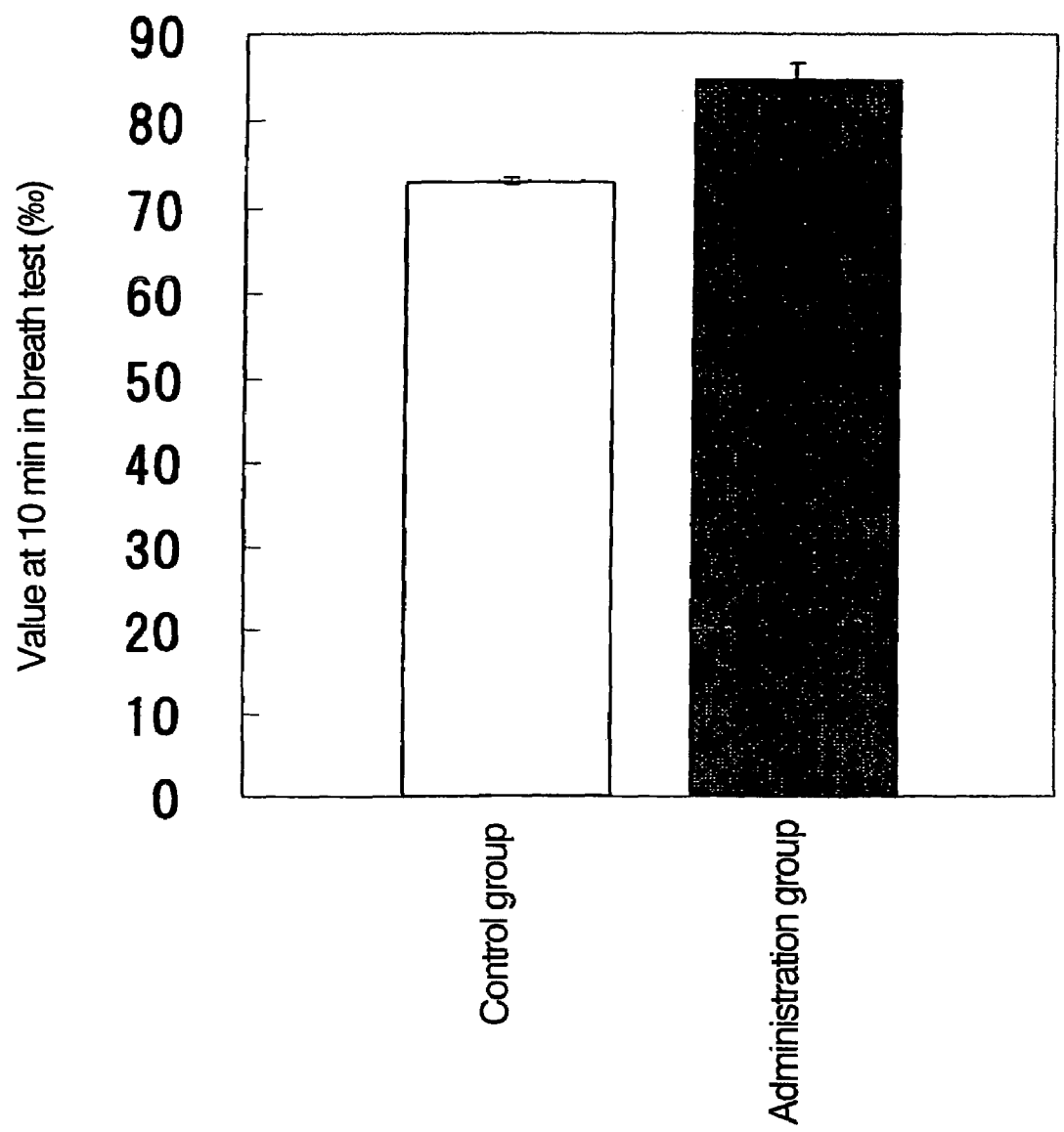
FIG. 9 shows the comparison of the values at the time point of 10 minutes in the [1,2-$^{13}$C]ornithine breath test.

The pharmacological effect of chlorpheniramine maleate is the inhibition of H1 receptor. The time course of the degree of increase of the $^{13}$C level in exhaled $CO_2$ ($\Delta^{13}$C (‰)) after the administration of [1,2-$^{13}$C]ornithine was measured and compared in the same manner as in Example 2 on rats which were administered with chlorpheniramine maleate (Sigma) intraperitoneally once on the day before the experiment and once on the day of the experiment (40 mg/kg each) and additionally administered with [1,2-$^{13}$C]ornithine (10 mg/kg) through the femoral vein 1 hour and 30 minutes after the last administration (administration group) and rats which were administered with [1,2-$^{13}$C]ornithine alone through the femoral vein (control group). The results of the [1,2-$^{13}$C] ornithine breath test were as follows: in the control group (n=2), the $\Delta^{13}$C increased rapidly until the time point of 5 minutes after the administration, then became to increase very slowly, and reached 73.1±0.4‰10 minutes after the administration; in the administration group (n=2), the $\Delta^{13}$C increased rapidly until the time point of 5 minutes after the administration, and reached 84.7±1.9‰10 minutes after the administration; thus, the $\Delta^{13}$C increased in the administration group (FIG. 9). From the results, the presence or absence of administration of chlorpheniramine maleate could be determined under the [1,2-$^{13}$C]ornithine administration conditions of the present example. Accordingly, by using [1,2-$^{13}$C]ornithine as a pharmacological effect diagnostic reagent, it becomes possible to evaluate the pharmacological effect of chlorpheniramine maleate. In addition, by using [1,2-$^{13}$C] ornithine as a screening reagent, it becomes possible to provide the method and the reagent for screening for an H1-receptor-targeting pharmaceutical agent having stronger effect and high stronger effect, medicative efficacy and/or a prodrug thereof.

All publications, patents and patent applications cited herein are incorporated herein by reference in their entity.

INDUSTRIAL APPLICABILITY

It is possible to evaluate the pharmacological effect of a medicine on its target independently on a real-time basis; this has been impracticable by any prior art technique.

It is also possible to evaluate the degree of inhibition of a target in a whole body and on a real-time basis; this has also been impracticable by any prior art technique. By utilizing the results of this evaluation, it is possible to screen for high medicative efficacy and/or a small side effect among pharmaceutical agents and/or prodrugs thereof.

What is claimed is:

1. A method of evaluating a pharmacological effect of a medicine, comprising:
    administering to a subject the medicine together with a diagnostic reagent comprising any one of the following substances:
        a first compound which serves as a substrate for an enzyme contained in the medicine to be evaluated or for an enzyme generated from a prodrug contained in the medicine to be evaluated, or a pharmaceutically acceptable salt thereof;
        a second compound which serves as a substrate for an enzyme which is directly inhibited by an enzyme inhibitor contained in the medicine to be evaluated or by an enzyme inhibitor generated from a prodrug contained in the medicine to be evaluated, or a pharmaceutically acceptable salt thereof;
        a third compound which serves as a substrate for an enzyme whose activity is altered by the binding between a receptor and a receptor ligand contained in the medicine to be evaluated or a receptor ligand generated from a prodrug contained in the medicine to be evaluated, or a pharmaceutically acceptable salt thereof; or
        a labeled form of any one of the first, second, or third compound or any salts thereof;
    collecting a biological sample from the subject at least once;
    measuring the amount of the any one of the first to third compounds, a pharmaceutically acceptable salt thereof, or a metabolite thereof in the biological sample; and
    evaluating the pharmacological effect of the medicine based on the amount obtained in the measurement step.

2. The method according to claim 1, wherein the diagnostic reagent comprises a $^{13}$C-labeled form of any one of the compounds or salts thereof and the $^{13}$ level in exhaled $CO_2$ in the subject is measured.

3. The method according to claim 1, wherein the medicine administered together with the first compound comprises amylase.

4. The method according to claim 1, wherein the first compound administered together with the medicine comprises [U-$^{13}$C]γ-cyclodextrin.

5. The method according to claim 1, wherein the medicine administered together with the second compound comprises dihydroxyphenylalanine (DOPA) decarboxylase.

6. The method according to claim 1, wherein the second compound administered together with the medicine comprises $^{13}$C-DOPA.

7. The method according to claim 1, wherein the medicine administered together with the second compound comprises α-glucosidase.

8. The method according to claim 1, wherein the second compound administered together with the medicine comprises $^{13}$C-Glc-Glc.

9. The method according to claim 1, wherein the medicine administered together with the second compound comprises a pancreatic protease.

10. The method according to claim 1, wherein the second compound administered together with the medicine comprises $^{13}$C-Bz-Arg-Ala.

11. The method according to claim 1, wherein the medicine administered together with the third compound comprises an ornithine metabolic enzyme.

12. The method according to claim 1, wherein the third compound administered together with the medicine comprises $^{13}$C-orinithine.

13. A method of screening pharmaceutical agents each comprising an enzyme, an enzyme inhibitor or a receptor ligand and/or prodrugs of the pharmaceutical agents, the method comprising:
    selecting a pharmaceutical agent or prodrug to be evaluated from pharmaceutical agents each comprising an enzyme, an enzyme inhibitor or a receptor ligand and/or prodrugs of the pharmaceutical agents;
    administering to a non-human subject the pharmaceutical agent or prodrug to be evaluated and a reagent comprising any one of the following substances:

a first compound which serves as a substrate for the enzyme which is included in the pharmaceutical agent to be evaluated or for an enzyme generated from the prodrug to be evaluated, or a pharmaceutically acceptable salt thereof;

a second compound which serves as a substrate for an enzyme which is directly inhibited by the enzyme inhibitor which is included in the pharmaceutical agent to be evaluated or by an enzyme inhibitor generated from the prodrug to be evaluated, or a pharmaceutically acceptable salt thereof;

a third compound which serves as a substrate for an enzyme whose activity is altered by the binding between a receptor and the receptor ligand which is included in the pharmaceutical agent to be evaluated or a receptor ligand generated from the prodrug to be evaluated, or a pharmaceutically acceptable salt thereof; or a labeled form of any one of the first, second, and third compounds or salts thereof;

collecting a biological sample from the subject at least once;

measuring the amount of the any one of the first, second, and third compounds or salts thereof or a metabolite thereof in the biological sample; and evaluating the pharmacological effect of the pharmaceutical agent or prodrug to be evaluated based on the amount obtained in the measurement step.

14. The method according to claim 13, wherein the reagent comprises a $^{13}$C-labeled form of any one of the first, second, and third compounds or salts thereof and the $^{13}$C level in exhaled $CO_2$ in the subject is measured.

15. The method according to claim 13, wherein the medicine administered together with the first compound comprises amylase.

16. The method according to claim 13, wherein the first compound administered together with the medicine comprises [U-$^{13}$C]γ-cyclodextrin.

17. The method according to claim 13, wherein the medicine administered together with the second compound comprises DOPA decarboxylase.

18. The method according to claim 13, wherein the second compound administered together with the medicine comprises $^{13}$C-DOPA.

19. The method according to claim 13, wherein the medicine administered together with the second compound comprises α-glucosidase.

20. The method according to claim 13, wherein the second compound administered together with the medicine comprises $^{13}$C-Glc-Glc.

21. The method according to claim 13, wherein the medicine administered together with the second compound comprises a pancreatic protease.

22. The method according to claim 13, wherein the second compound administered together with the medicine comprises $^{13}$C-Bz-Arg-Ala.

23. The method according to claim 13, wherein the medicine administered together with the third compound comprises an ornithine metabolic enzyme.

24. The method according to claim 13, wherein the third compound administered together with the medicine comprises $^{13}$C-orinithine.

25. A method of screening pharmaceutical agents, comprising:

selecting a pharmaceutical agent or prodrug to be evaluated from pharmaceutical agents each comprising an enzyme, an enzyme inhibitor or a receptor ligand and/or prodrugs of the pharmaceutical agents;

administering to a non-human subject the pharmaceutical agent or prodrug to be evaluated and a reagent comprising:

a first compound which serves as a substrate for the enzyme which is included in the pharmaceutical agent to be evaluated or for an enzyme generated from the prodrug to be evaluated, or a pharmaceutically acceptable salt thereof;

a second compound which serves as a substrate for a different enzyme whose activity is coupled to an activity of the enzyme which is included in the pharmaceutical agent to be evaluated oran activity of an enzyme generated from the prodrug to be evaluated, or a pharmaceutically acceptable salt thereof;

a third compound which serves as a substrate for an enzyme which is directly inhibited by the enzyme inhibitor which is included in the pharmaceutical agent to be evaluated or by an enzyme inhibitor generated from the prodrug to be evaluated, or a pharmaceutically acceptable salt thereof;

a fourth compound which serves as a substrate for an enzyme whose activity is coupled to an activity of an enzyme inhibitor for another enzyme, where the enzyme inhibitor is included in the pharmaceutical agent to be evaluated or coupled to an activity of an enzyme inhibitor generated from the prodrug to be evaluated, or a pharmaceutically acceptable salt thereof;

a fifth compound which serves as a substrate for an enzyme whose activity is altered by the binding between a receptor and the receptor ligand which is included in the pharmaceutical agent to be evaluated or a receptor ligand generated from the prodrug to be evaluated, or a pharmaceutically acceptable salt thereof; or a labeled form of any one of the first to fifth compounds, wherein the enzyme for which the first compound is a substrate comprises amylase, the enzyme for which the third compound is a substrate comprises dihydroxyphenvialanine (DOPA) decarboxylase, α-glucosidase, or pancreatic protease, or the enzyme for which the fifth compound is a substrate comprises an ornithine metabolic enzyme;

collecting a biological sample from the subject at least once;

measuring the amount of the any one of the first to fifth compounds, a pharmaceutically acceptable salt thereof, or a metabolite thereof in the biological sample; and evaluating the pharmacological effect of the pharmaceutical agent or prodrug to be evaluated based on the amount obtained in the measurement step.

26. The method according to claim 25, wherein the reagent comprises a $^{13}$C-labeled form of any one of the first to fifth compounds or a pharmaceutically acceptable salt thereof, and the $^{13}$C level in exhaled $CO_2$ in the subject is measured.

* * * * *